(12) United States Patent
Greenhalgh et al.

(10) Patent No.: US 12,226,299 B2
(45) Date of Patent: Feb. 18, 2025

(54) TEXTURED MEDICAL TEXTILES

(71) Applicant: TELA Bio, Inc., Malvern, PA (US)

(72) Inventors: E. Skott Greenhalgh, Gladwyne, PA (US); John-Paul Romano, Chalfont, PA (US); Travis Speicher, Malvern, PA (US); Brendan Farrell, Malvern, PA (US)

(73) Assignee: TELA Bio, Inc., Malvern, PA (US)

( * ) Notice: Subject to any disclaimer, the term of this patent is extended or adjusted under 35 U.S.C. 154(b) by 232 days.

(21) Appl. No.: 17/932,856

(22) Filed: Sep. 16, 2022

(65) Prior Publication Data

US 2023/0008637 A1    Jan. 12, 2023

Related U.S. Application Data

(63) Continuation of application No. 16/813,522, filed on Mar. 9, 2020, now Pat. No. 11,446,130.

(60) Provisional application No. 62/816,040, filed on Mar. 8, 2019.

(51) Int. Cl.
    A61F 2/00     (2006.01)
    A61F 2/36     (2006.01)
    A61L 27/36    (2006.01)

(52) U.S. Cl.
    CPC ........ *A61F 2/0063* (2013.01); *A61L 27/3633* (2013.01); *A61F 2002/0068* (2013.01); *A61F 2210/0004* (2013.01); *A61F 2220/0075* (2013.01); *A61F 2230/0054* (2013.01); *A61F 2230/0093* (2013.01); *A61F 2240/001* (2013.01); *A61L 2430/34* (2013.01)

(58) Field of Classification Search
    CPC ............ A61F 2/0063; A61F 2002/0068; A61F 2210/0004; A61F 2220/0075; A61F 2230/0054; A61F 2240/001; A61F 2210/0076; A61L 27/3633; A61L 2430/34
    See application file for complete search history.

(56) References Cited

U.S. PATENT DOCUMENTS

| | | | |
|---|---|---|---|
| 2,259,025 | A | 10/1941 | Cosgro |
| 3,033,139 | A | 5/1962 | Tateishi |
| 3,054,406 | A | 9/1962 | Usher |
| 3,155,095 | A | 3/1964 | Brown |

(Continued)

FOREIGN PATENT DOCUMENTS

| | | |
|---|---|---|
| DE | 10312674 A1 | 10/2003 |
| DE | 112007001732 T5 | 4/2011 |

(Continued)

OTHER PUBLICATIONS

Deeken et al., Physiocomechanical evaluation of absorbable and nonabsorbable barrier composite meshes for laparoscopic ventral hernia repair. Surg. Endosc., 25(5), 1541-1552 ( 12 pages, Author Manuscript); May 2011.

(Continued)

*Primary Examiner* — Suzette J Gherbi
(74) *Attorney, Agent, or Firm* — Shay Glenn LLP

(57) ABSTRACT

Described herein are implants (e.g., medical textiles/biotextiles) that include stitched gripping filaments to increase gripping, and methods of forming and using them. In some configurations these apparatuses may be configured as surgical grafts that may be used for soft tissue reconstruction, regeneration, or repair.

22 Claims, 17 Drawing Sheets

(56) References Cited

U.S. PATENT DOCUMENTS

| | | |
|---|---|---|
| 3,364,200 A | 1/1968 | Ashton et al. |
| 3,658,023 A | 4/1972 | Rossi |
| 4,466,370 A | 8/1984 | Eguchi et al. |
| 5,593,441 A | 1/1997 | Lichtenstein et al. |
| 5,634,931 A | 6/1997 | Kugel |
| 5,683,400 A | 11/1997 | McGuire |
| 5,707,395 A | 1/1998 | Li |
| 5,723,010 A | 3/1998 | Yui et al. |
| 5,919,232 A | 7/1999 | Chaffringeon et al. |
| 5,990,378 A | 11/1999 | Ellis |
| 6,120,539 A | 9/2000 | Eldridge et al. |
| 6,258,124 B1 | 7/2001 | Darois et al. |
| 6,319,264 B1 | 11/2001 | Törmälä et al. |
| 6,371,985 B1 | 4/2002 | Goldberg |
| 6,383,201 B1 | 5/2002 | Dong |
| 6,652,595 B1 | 11/2003 | Nicolo |
| 6,814,748 B1 | 11/2004 | Baker et al. |
| 6,962,120 B1 | 11/2005 | Fujikura et al. |
| 7,824,420 B2 | 11/2010 | Eldridge et al. |
| 7,946,236 B2 | 5/2011 | Butcher |
| 8,074,591 B2 | 12/2011 | Butcher et al. |
| 8,182,545 B2 | 5/2012 | Cherok et al. |
| 8,236,342 B2 | 8/2012 | Thomas et al. |
| 8,853,294 B2 | 10/2014 | Myung et al. |
| 9,205,052 B2 | 12/2015 | Kim et al. |
| 9,289,279 B2 | 3/2016 | Wilson et al. |
| 9,295,757 B2 | 3/2016 | Patel et al. |
| 9,326,840 B2 | 5/2016 | Mortarino |
| 9,364,310 B2 | 6/2016 | Stopek |
| 9,421,079 B2 | 8/2016 | Koullick et al. |
| 9,468,705 B2 | 10/2016 | Geller |
| 9,510,925 B2 | 12/2016 | Hotter et al. |
| 9,554,887 B2 | 1/2017 | Lecuivre |
| 9,585,838 B2 | 3/2017 | Hartounian et al. |
| 9,770,414 B2 | 9/2017 | Garcia et al. |
| 9,775,700 B2 | 10/2017 | Greenhalgh et al. |
| 9,820,843 B2 | 11/2017 | Greenhalgh et al. |
| 9,925,030 B2 | 3/2018 | Greenhalgh et al. |
| 10,130,457 B2 | 11/2018 | Greenhalgh et al. |
| 10,213,284 B2 | 2/2019 | Greenhalgh et al. |
| 10,426,587 B2 | 10/2019 | Greenhalgh et al. |
| 10,500,030 B2 | 12/2019 | Greenhalgh et al. |
| 10,561,485 B2 * | 2/2020 | Greenhalgh .......... A61L 31/005 |
| 10,675,141 B2 | 6/2020 | Greenhalgh et al. |
| 10,702,364 B2 | 7/2020 | Greenhalgh et al. |
| 11,344,397 B2 | 5/2022 | Greenhalgh et al. |
| 11,369,464 B2 | 6/2022 | Greenhalgh et al. |
| 11,446,130 B2 | 9/2022 | Greenhalgh et al. |
| 11,464,616 B2 | 10/2022 | Greenhalgh et al. |
| 2001/0020188 A1 | 9/2001 | Sander |
| 2002/0111392 A1 | 8/2002 | Cruise |
| 2003/0023316 A1 | 1/2003 | Brown et al. |
| 2003/0225355 A1 * | 12/2003 | Butler ................ A61F 2/0063 602/48 |
| 2004/0010320 A1 | 1/2004 | Huckle et al. |
| 2004/0033212 A1 | 2/2004 | Thomson et al. |
| 2004/0054376 A1 | 3/2004 | Ory et al. |
| 2004/0078089 A1 | 4/2004 | Ellis et al. |
| 2004/0138762 A1 | 7/2004 | Therin et al. |
| 2004/0249457 A1 | 12/2004 | Smith et al. |
| 2005/0070930 A1 | 3/2005 | Kammerer |
| 2005/0113849 A1 | 5/2005 | Popadiuk et al. |
| 2005/0113938 A1 | 5/2005 | Jamiolkowski et al. |
| 2005/0118236 A1 | 6/2005 | Qiu et al. |
| 2005/0255543 A1 | 11/2005 | Just et al. |
| 2006/0178683 A1 | 8/2006 | Shimoji et al. |
| 2006/0217747 A1 | 9/2006 | Ferree |
| 2006/0229722 A1 | 10/2006 | Bianchi et al. |
| 2007/0088434 A1 | 4/2007 | Frank |
| 2007/0190108 A1 | 8/2007 | Datta et al. |
| 2007/0224238 A1 | 9/2007 | Mansmann et al. |
| 2008/0097601 A1 | 4/2008 | Codori-Hurff et al. |
| 2008/0167729 A1 | 7/2008 | Nelson et al. |
| 2008/0181928 A1 | 7/2008 | Hakimi-Mehr et al. |
| 2009/0018655 A1 | 1/2009 | Brunelle et al. |
| 2009/0054339 A1 | 2/2009 | Marshall et al. |
| 2009/0069893 A1 | 3/2009 | Paukshto et al. |
| 2009/0082864 A1 | 3/2009 | Chen et al. |
| 2009/0216338 A1 | 8/2009 | Gingras et al. |
| 2009/0306688 A1 | 12/2009 | Patel et al. |
| 2009/0326577 A1 | 12/2009 | Johnson et al. |
| 2010/0010114 A1 | 1/2010 | Myung et al. |
| 2010/0028396 A1 | 2/2010 | Ward et al. |
| 2010/0063599 A1 | 3/2010 | Brunelle et al. |
| 2010/0100107 A1 | 4/2010 | Duggal et al. |
| 2010/0120679 A1 | 5/2010 | Xu et al. |
| 2010/0217388 A1 | 8/2010 | Cohen et al. |
| 2010/0249929 A1 | 9/2010 | Kurz et al. |
| 2010/0305500 A1 | 12/2010 | Lambert et al. |
| 2010/0318108 A1 | 12/2010 | Datta et al. |
| 2010/0318124 A1 | 12/2010 | Leung et al. |
| 2011/0014153 A1 | 1/2011 | Derwin et al. |
| 2011/0020420 A1 * | 1/2011 | Bosley, Jr. .......... A61L 27/3633 623/23.72 |
| 2011/0125287 A1 | 5/2011 | Hotter et al. |
| 2011/0196490 A1 | 8/2011 | Gadikota et al. |
| 2011/0250264 A1 | 10/2011 | Schutt et al. |
| 2011/0257761 A1 | 10/2011 | Mortarino |
| 2011/0301717 A1 | 12/2011 | Becker |
| 2012/0010637 A1 | 1/2012 | Stopek et al. |
| 2012/0035608 A1 | 2/2012 | Marchitto et al. |
| 2012/0082712 A1 | 4/2012 | Stopek et al. |
| 2012/0095482 A1 | 4/2012 | Peterson et al. |
| 2012/0143329 A1 | 6/2012 | Kim |
| 2012/0165957 A1 | 6/2012 | Everland et al. |
| 2012/0179176 A1 | 7/2012 | Wilson et al. |
| 2012/0184974 A1 | 7/2012 | Becker |
| 2012/0253464 A1 | 10/2012 | Hwang et al. |
| 2013/0064772 A1 | 3/2013 | Swiss et al. |
| 2013/0116799 A1 | 5/2013 | Derwin et al. |
| 2013/0172994 A1 | 7/2013 | Becker |
| 2013/0197300 A1 | 8/2013 | Koullick et al. |
| 2013/0209547 A1 | 8/2013 | Garcia et al. |
| 2013/0211307 A1 | 8/2013 | Evans et al. |
| 2013/0267137 A1 | 10/2013 | Peniston et al. |
| 2013/0303958 A1 | 11/2013 | Holm et al. |
| 2013/0304098 A1 | 11/2013 | Mortarino |
| 2013/0317286 A1 | 11/2013 | Bluecher et al. |
| 2014/0090942 A1 | 4/2014 | Schlipper |
| 2014/0094931 A1 | 4/2014 | Derwin et al. |
| 2014/0276993 A1 | 9/2014 | Reilly et al. |
| 2014/0364878 A1 | 12/2014 | Ladet et al. |
| 2015/0112434 A1 | 4/2015 | Felix et al. |
| 2015/0127103 A1 | 5/2015 | Seedhom |
| 2015/0267330 A1 | 9/2015 | Carrier et al. |
| 2015/0297798 A1 | 10/2015 | Badylak et al. |
| 2016/0058534 A1 | 3/2016 | Derwin et al. |
| 2016/0058589 A1 * | 3/2016 | Bar ...................... A61L 31/06 623/1.15 |
| 2016/0136289 A1 | 5/2016 | Puri et al. |
| 2016/0206580 A1 | 7/2016 | Los et al. |
| 2016/0262208 A1 | 9/2016 | Hsieh |
| 2016/0374791 A1 | 12/2016 | Lecuivre et al. |
| 2017/0027678 A1 * | 2/2017 | Greenhalgh .......... A61L 31/005 |
| 2017/0027679 A1 | 2/2017 | Serban et al. |
| 2017/0086972 A1 | 3/2017 | Braido et al. |
| 2017/0245847 A1 | 8/2017 | Obermiller et al. |
| 2019/0008623 A1 | 1/2019 | Nemoto et al. |
| 2019/0380822 A1 * | 12/2019 | Greenhalgh .......... A61L 31/048 |
| 2020/0238604 A1 * | 7/2020 | Hart ...................... A61F 2/0063 |
| 2020/0297476 A1 | 9/2020 | Greenhalgh et al. |
| 2020/0330211 A1 | 10/2020 | Greenhalgh et al. |
| 2020/0360129 A1 | 11/2020 | Moses et al. |
| 2020/0397949 A1 * | 12/2020 | Greenhalgh ............ A61L 27/56 |
| 2021/0030925 A1 * | 2/2021 | Lopez .................... A61L 27/48 |
| 2021/0093444 A1 | 4/2021 | Feinberg et al. |
| 2021/0290416 A1 * | 9/2021 | Hall ........................ A61L 27/18 |
| 2022/0110749 A1 | 4/2022 | Hariton et al. |
| 2022/0133465 A1 * | 5/2022 | Rocco .................... A61L 27/56 600/37 |
| 2022/0273412 A1 | 9/2022 | Greenhalgh et al. |
| 2022/0296350 A1 | 9/2022 | Greenhalgh et al. |

(56) References Cited

U.S. PATENT DOCUMENTS

2023/0277287 A1    9/2023  Greenhalgh et al.
2023/0293281 A1*   9/2023  Greenhalgh .............. A61F 2/12
                                                      623/8
2023/0338637 A1   10/2023  Nazerali et al.

FOREIGN PATENT DOCUMENTS

| EP | 2198854 A2 | 6/2010 |
| EP | 2229918 A1 | 9/2010 |
| EP | 2300066 A2 | 3/2011 |
| EP | 2344133 A2 | 7/2011 |
| RU | 2524196 C2 | 7/2014 |
| WO | WO00/57812 A1 | 10/2000 |
| WO | WO02/078568 A1 | 10/2002 |
| WO | WO03/082363 A1 | 10/2003 |
| WO | WO03/094781 A1 | 11/2003 |
| WO | WO2008/095038 A1 | 8/2008 |
| WO | WO2012/017415 A2 | 2/2012 |
| WO | WO2017/050837 A1 | 3/2017 |
| WO | WO2017/191276 A1 | 11/2017 |
| WO | WO2017/223462 A1 | 12/2017 |

OTHER PUBLICATIONS

Franklin et al.; Uptake of tetracycline by aortic aneurysm wall and its effect on inflammation and proteolysis; British Journal of Surgery; 86(6); pp. 771-775; Jun. 1999.

Mayo Clinic; Placement of Breast Implants; retrieved May 25, 2017 from http://www.mayoclinic.org/placement-of-breast-implants/img-20007384; 1 pg; May 25, 2017.

Pyo et al.; Targeted gene disruption of matrix metalloproteinase-9 (gelatinase B) suppresses development of experimental abdominal aortic aneurysms; The journal of Clinical Investigation; 105(11); pp. 1641-1649; Jun. 2000.

Tambiah et al.; Provocation of experimental aortic inflammation and dilatation by inflammatory mediators and chlamydia pneumoniae; British Journal of Surgery; 88(7); pp. 935-940; Jul. 2001.

Walton et al.; Inhibition of prostoglandin E2 synthesis in abdominal aortic; Circulation; 100; pp. 48-54, 8 pages; Jul. 1999.

Xu et al.; Sp1 increases expression of cyclooxygenase-2 in hypoxic vascular endothelium implications for the mechanisms of aortic aneurysm and heart failure; journal of Biological Chemistry; 275(32); pp. 24583-24589; Aug. 2000.

Greenhalgh ; U.S. Appl. No. 18/157,653 entitled "Surgical repair graft," filed Jan. 20, 2023.

Nazerali; U.S. Appl. No. 17/447,166 entitled "Subcutaneous and pocket irrigator," filed Sep. 8, 2021.

Romano et al.; U.S. Appl. No. 18/353,858 entitled "Nonuniform embroidered soft tissue implant structure," filed Jul. 17, 2023.

Greenhalgh et al.; U.S. Appl. No. 18/511,680 entitled "Corner-lock stitch patterns," filed Nov. 16, 2023.

Greenhalgh et al.; U.S. Appl. No. 18/664,253 entitled "Surgical repair graft," filed May 14, 2024.

* cited by examiner

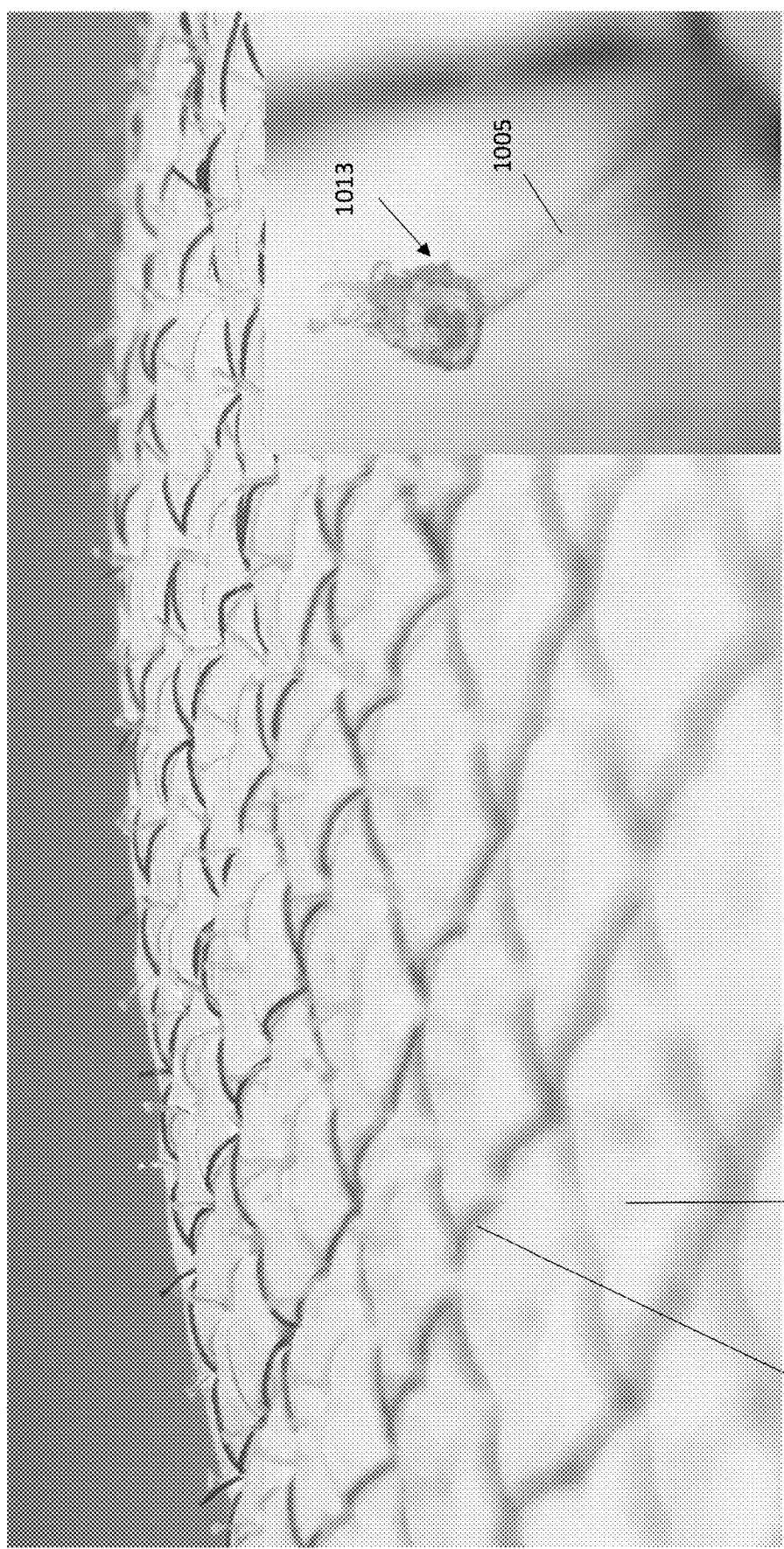

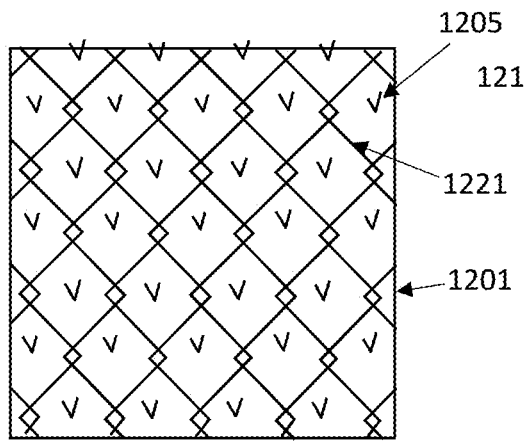
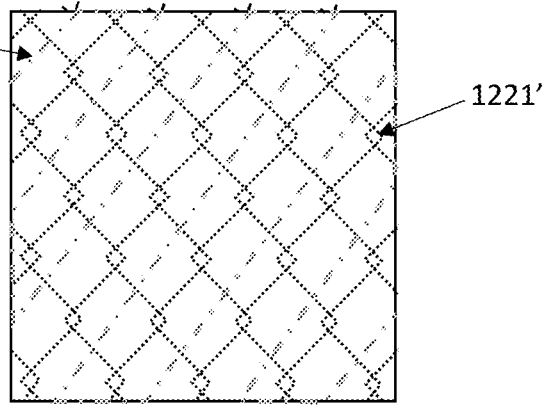
FIG. 12A
FIG. 12B
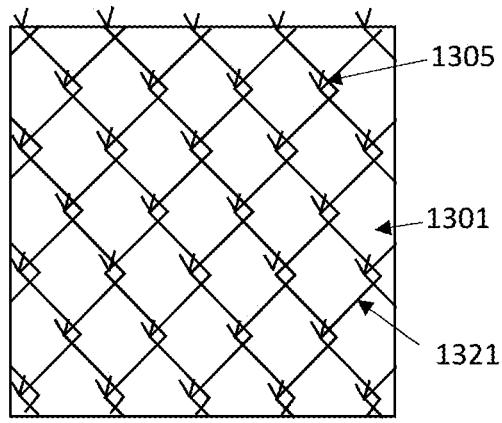
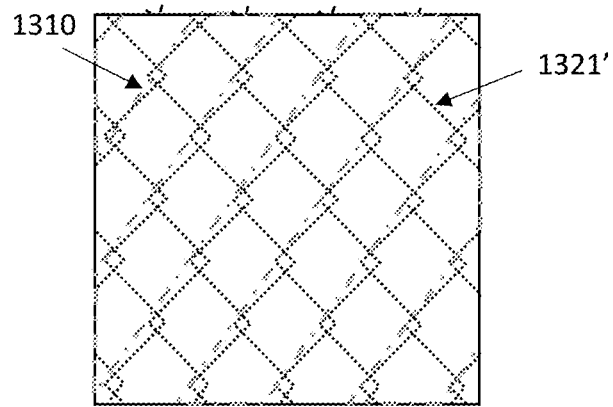
FIG. 13A
FIG. 13B

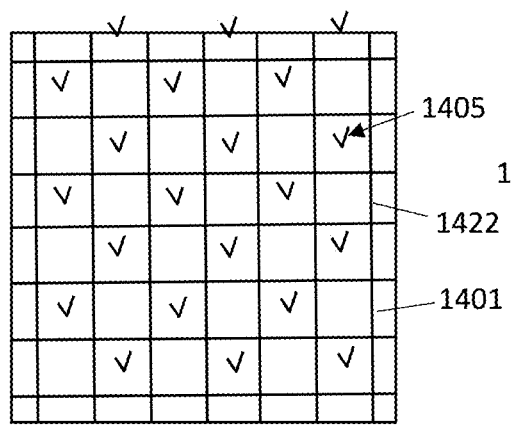 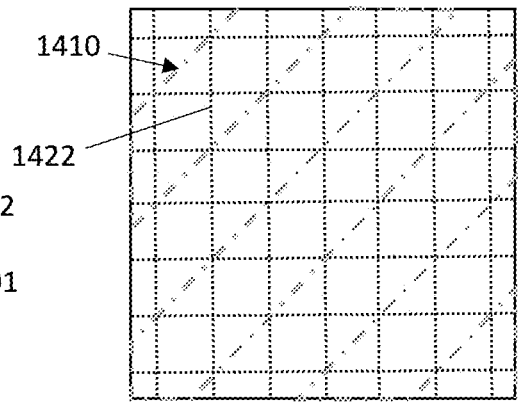
FIG. 14A  FIG. 14B
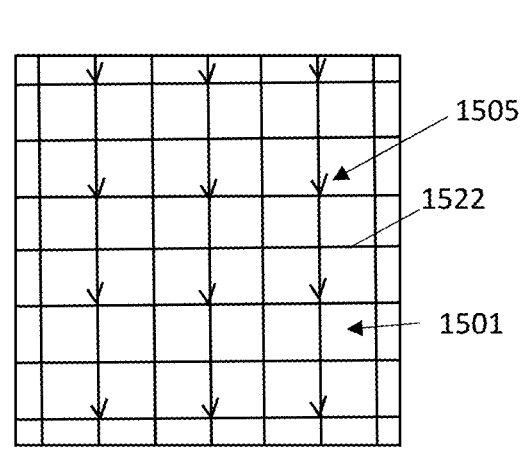 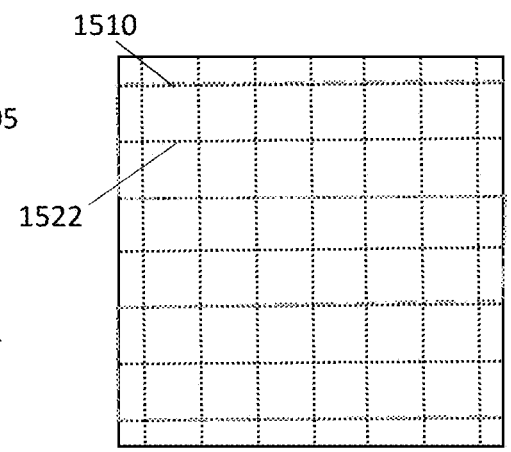
FIG. 15A  FIG. 15B

TEXTURED MEDICAL TEXTILES

CROSS REFERENCE TO RELATED APPLICATIONS

This patent application is a continuation of patent application Ser. No. 16/813,522, titled "TEXTURED MEDICAL TEXTILES" filed Mar. 9, 2020, now U.S. Patent Publication No. 2020/0281707 which claims priority to U.S. Provisional Patent Application No. 62/816,040, titled "TEXTURED MEDICAL TEXTILES" and filed on Mar. 8, 2019; this application is herein incorporated by text in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relates generally to surgical grafts and medical textiles useful for soft tissue reconstruction, regeneration, or repair. More particularly, described herein are surgical repair grafts and medical textiles for soft tissue repair that include a textured surface formed by a sewn material which may add a substantial gripping force while advantageously matching the biomechanical properties of tissue during healing and recovery.

BACKGROUND

Soft tissues within a body may benefit from repair or reinforcement due to a variety of reasons such as disease, enhancement, or trauma.

An implant or medical textile may be used to repair or reinforce a soft tissue such as an unhealthy or modified tissue in the body. The tissue may be, for example, tissue that is no longer able to maintain its shape or physiological function such as a hernia or a tissue for which a shape or size change is desired such as breast size or shape change due to breast enhancement or breast reconstruction. A hernia is a condition in which part of an organ or fatty tissue protrudes through the wall of a surrounding tissue. Abdominal wall hernia surgery is one of the most common surgical procedures, and according to the U.S. Food and Drug Administration, more than 1 million hernia repairs are performed in the United States alone. Common adverse events associated with hernia repair surgery include pain, infection, hernia recurrence, adhesion formation, obstruction, bleeding, and fluid build-up. Breast reconstruction may be performed to reconstruct a breast after a mastectomy has been performed to remove a diseased due to cancer or as a prophylactic measure to prevent cancer. Common adverse events associated with breast reconstruction include infection, pain, delayed healing, and swelling.

There is a need for improved surgical repair materials and medical textiles.

SUMMARY OF THE DISCLOSURE

Described herein are apparatuses (e.g., devices and system, including implants) and methods of making and using these apparatuses, having increased gripping strength. These apparatuses (e.g., implants) may include surgical grafts and medical textiles. In general, these implants may have a textured and/or gripping surface that is formed by a sewn material, such as a filament or plurality of filaments into one or more layers of a biotextile (biologic) or medical textile (polymer based). In some variations the resulting surface includes a plurality of gripping strands, which may be referred to herein as gripping filaments, posts and/or projections, formed by the sewn material. The density, distribution, size and spacing (arrangement) of the gripping strands may therefore be formed by sewing or stitching (e.g., using a sewing machine) into the biotextile/medical textile. These materials typically have a high grip strength, particular when abutting an irregular surface.

The resulting gripping strands may beneficially include both the projecting body of the gripping strand, as well as an attachment to a second (continuous) strand or filament that extends on the opposite side of the implant (e.g., the one or more sheets of the surgical graft or medical textile. The second strand may be an elongate, continuous strand that couples to a plurality of these gripping strands at a vertex, and extends along the bottom surface of the implant, providing a secure, yet flexible attachment to the textile. As will be described in greater detail below, the surgical graft/medical textile may in particular be one or more sheets of extracellular matrix material (e.g., collagen). In general, the flexibility and compliance of the implant may be important in providing beneficial physiological properties to the implant, effecting both the resulting feel of the implant, as well as the ability of the patient to heal following insertion of the implant, and the strength and mechanical properties of the implant. The use of gripping strands extending from a first side of the implant that are coupled (e.g., stitched) to at least one length a continuous strand of material on an opposite side of the implant may permit the plurality of gripping strands to increase the gripping strength of the first side, while distributing the gripping force along the opposite side of the implant, and dynamically modifying the compliance of the implant.

Furthermore, any of the implants described herein may include or incorporate (including incorporating into the pattern of gripping strands) one or more stitching patterns through the sheet(s) of material forming the implant. For example, a stitching pattern forming a mesh, including but not limited to an interlocking mesh and/or a compliance control stitching pattern, may be included along with the sewn gripping strands. In some variations the continuous strand of material to which the plurality of strands is coupled (and from which they may extend) may be part of a stitching pattern (including a grid pattern). Alternatively or additionally, a stitching pattern may be added after forming the plurality of gripping strands, as will be described in greater detail herein.

Any of the implants (e.g., implant materials, medical textiles and/or biotextiles) described herein may be formed into a surgical repair graft and/or may include one or a plurality of stacked layers. The implant (and individual layers of the implant) may be porous, e.g., having a plurality of openings. In some implants, the substrate (e.g., the sheet or sheets) may be referred to as a carrier matrix and may include a porous covering having a porosity of at least 100 pores per square inch (PPI). In some implants the carrier matrix may include a porous covering having a porosity of between 10 pores per square inch (PPI) and 100 pores per square inch. In some implants, the substrate may have a porosity of at least 100 pores per square inch (PPI). The implant substrate may have a porosity of between, e.g., 10 pores per square inch (PPI) and 100 pores per square inch. In any of these implants, at least one biotextile layer may have an open cell pore of between 0.5 mm and 6 mm diameter. Any of these substrate may be a biotextile layer; any of these substrates may be, e.g., an extracellular matrix material. For example, any of these substrates may be a collagen material.

As mentioned, the implants may further include one or more compliance control stitching patterns. Some of these surgical repair grafts may further include patterns sewn or embroidered into the implant (e.g., graft, such as a hernia graft). Some of these surgical repair implants may further include one or more compliance control stitch patterns including monofilament thread or yarns including polyethylene or polypropylene sewn or embroidered into the graft. In general the stands of material forming the plurality of gripping strands and/or the strand (e.g., continuous strand) to which the gripping strands is attached, as well as the one or more strands forming the compliance-modifying stitching patterns (e.g., corner-lock stitching patterns) may be formed of one or more filaments (monofilaments or filament bundles) of material, such as polymeric materials (e.g., polyethylene and/or polypropylene). Any of these filaments may be bioresorable and/or non-bioresorbable. In particular, it may be beneficial to provide the plurality of gripping strands that are formed of a bioresorbable material, which may be resorbed by the body over time after implantation at a different rate than other portions of the implant, including the substrate and or other stitching pattern(s).

Any of the implants described herein may be configured so that the compliance of the implant is modified and/or controlled by the stitching, including the stitching of the continuous gripping strands (and the strand to which the gripping strands are attached on the opposite side of the implant) and/or the stitching pattern, such as a grid stitching pattern (e.g., a corner-lock stitch stitching pattern, etc.). In general, the compliance of the implants described herein may be modified by the gripping strands and one or more compliance control stitch patterns sewn or embroidered into the graft so that the compliance strain of the implant is between about 10-30% at 16 N/cm.

As mentioned above, the substrate forming the implant (e.g., the biotextile layer) may include extracellular matrix, which may be naturally occurring or may be synthetic. In some of these implants, the substrate includes at least on sheet of a biotextile layer formed of an extracellular matrix material (ECM) such as (but not limited to) collagen. In some of these implants the substrate, which may also be referred to as a carrier matrix, may formed of two or more sheets (e.g., of biotextile layers) that are sewn together, including by a stitching pattern (such as a grid pattern sewn into the substrate). For example, multiple layers of ECM may be flexibly attached to each other by a pattern of discrete attachment sites (including in particular sewn attachment sites) having a density of attachment sites that is less than about 10 attachments/mm$^2$ (e.g., between 10 attachment sites/mm$^2$ and 100 attachment sites/mm$^2$, e.g., fewer than about 10 attachments/mm$^2$, between 10 attachments/mm$^2$ and 100 attachments/mm$^2$, etc.).

The compliance of the implant, once implanted, may increase over time when the exposed to an aqueous solution. In some of these implants, the compliance of the implant may increase over time when the carrier matrix is exposed to an aqueous solution and the substrate (e.g., biotextile layer(s)) remain intact. In any of these implants described herein, the compliance of the surgical repair graft may change or increase by less than 1%, less than 5% or less than 10% when the carrier matrix is continuously exposed to a bodily fluid for 1 day, 1 week, 2 weeks, 4 weeks, 6 weeks, or 12 weeks. In some of these surgical repair grafts a compliance of the surgical repair graft may differ by less than 20% compared with the compliance of similarly stacked layers without carrier matrix when the grafts are continuously exposed to a bodily fluid for 12 weeks. In some of these surgical repair grafts a compliance of the surgical repair graft may differ by less than 5% compared with the compliance of similarly stacked layers without carrier matrix when the grafts are continuously exposed to a bodily fluid for 12 weeks. In some of these surgical repair grafts a difference in uniaxial tension of the surgical repair graft may change by less than 20% when the carrier matrix is adhered thereto compared with the uniaxial tension of a similar surgical repair without carrier matrix. In some of these surgical repair grafts a difference in uniaxial tension of the surgical repair may change by less than 5% when the carrier matrix is adhered thereto compared with the uniaxial tension of a similar surgical repair graft without carrier matrix. In some of these surgical repair grafts a difference in bending stiffness of the surgical repair graft may change by less than 20% when the carrier matrix is adhered thereto compared with the bending stiffness of a similar surgical repair graft without carrier matrix. In some of these surgical repair grafts a bending stiffness of the surgical repair graft may change by less than 5% when the carrier matrix is adhered thereto compared with the axial tensile modulus of a similar surgical repair graft without carrier matrix. In some of these surgical repair grafts a difference in burst strength of the surgical repair graft may change by less than 20% when the carrier matrix is adhered thereto compared with the burst strength of a similar surgical repair graft without carrier matrix. In some of these surgical repair grafts a difference in burst strength of the surgical repair graft may change by less than 5% when the carrier matrix is adhered thereto compared with the burst strength of a similar surgical repair graft without carrier matrix. In any of these surgical repair grafts a difference in surface roughness of the layers may change by less than 20% when the carrier matrix is adhered thereto compared with the burst strength of a similar surgical repair graft without carrier matrix. In some of these surgical repair grafts a difference in surface roughness of the layers may change by less than 20% when the carrier matrix is adhered thereto compared with the burst strength of a similar surgical repair graft without carrier matrix.

Thus, described herein are implants, such as surgical repair materials, surgical repair meshes (or scaffolds or patches), hernia meshes (or scaffolds or patches), etc., that have enhanced sheer, e.g., grip, strength. For example, any of these implants may include: a sheet of substrate material, such as one or more, e.g., a stack, of layers of extracellular material, including collagen; a first strand of material extending adjacent to a first side of the sheet of substrate material; a plurality of gripping strands extending proud of a second side of the sheet of substrate material, wherein each gripping strand of the plurality of gripping strands comprises one or more arms extending from a vertex in which the gripping strand is wrapped around the first strand of material extending on the first side of the sheet of substrate material; and a compliance control pattern stitched through the sheet of substrate material formed by a second strand of material and either the first strand or a third strand of material. The compliance control pattern may be a grid pattern, such as a corner lock stitch pattern. The grid pattern is typically a network of crossing stitches forming open regions; the open regions may be square or non-square, including trapezoidal, rhomboid, rectangular, triangular, pentagonal, etc.

In any of the apparatuses and methods described herein the gripping strand(s) may be slidably wrapped around the first strand of material. This may allow the gripping strands to slide slightly over the first strand. As the first strand extends along the back of the implant (e.g., in a continuous or semi-continuous length, spanning at least 2 or three, or more, vertices), this may allow distribution of the forces, including shear forces, acting on the individual arms of the gripping strands. The gripping strand may be slidably wrapped around the first strand so that it loops at least partially around the first strand. The vertex between an individual gripping strand and the first strand may be on the back side of the implant, or it may be pulled slightly into the substrate.

In general, as used herein a gripping strand may be a single arm or a pair of arms. For example, a V-shaped gripping strand may have two arms that are connected at the vertex, where they wrap around the first (back) strand. In variations having a single arm, the gripping strand forming the arm may wrap around the first strand and then extend from this vertex back up and across the top surface of the implant (e.g., adjacent to the top surface) to form a second gripping strand having a single arm that is laterally offset along the top surface.

For example, an implant may include: a sheet of substrate comprising extracellular matrix material (ECM); a continuous first strand of material extending adjacent to a first side of the ECM; a plurality of gripping strands extending proud of a second side of the ECM, wherein each gripping strand of the plurality of gripping strands comprises one or more arms extending from a vertex that is slidably wrapped around the continuous first strand of material extending on the first side of the ECM; and a grid pattern stitched through the sheet of ECM formed by a continuous second strand of material and either the continuous first strand, or a continuous third strand of material.

Thus, in some variations these implants may comprise: a substrate (e.g., a sheet of extracellular matrix material, ECM); a first strand of material extending adjacent to a first side of the substrate in a back-and-forth pattern; a plurality of gripping strands extending proud of a second side of the substrate, wherein each gripping strand of the plurality of gripping strands comprises one or more arms extending from a vertex that is wrapped around the continuous first strand of material extending on the first side of the substrate; and a pattern stitched through the substrate formed by a continuous second strand of material and either the first strand or a continuous third strand of material.

The first strand may be a single continuous strand, or multiple strands, each of which is attached to a plurality of the gripping strands (also referred to herein as posts) enhancing the gripping strength of the implant top surface (in this example, the second side of the substrate). As mentioned above, the substrate may be one or more sheets of biotextile such as ECM. The pattern stitched through the substrate may be, e.g., a grid pattern. In some variations the grid pattern includes one or more (e.g., a plurality of) lines of stitches that cross-over each other. In some variation the grid pattern is a corner-lock stitch pattern, as described in greater detail herein. In some variations the grid pattern is formed of one or more straight and/or curved stitched lines though the substrate.

For example, an implant may include: a sheet of extracellular matrix material (ECM); a continuous first strand of material extending adjacent to a first side of the ECM in a back-and-forth pattern; a plurality of V-shaped gripping strands extending proud of a second side of the ECM, wherein each V-shaped gripping strand of the plurality of V-shaped gripping strands comprises a pair of arms extending from a vertex that is wrapped around the continuous first strand of material extending on the first side of the ECM; and a grid pattern stitched through the sheet of ECM formed by a continuous second strand of material and a continuous third strand of material.

In any of the variations described herein the gripping strands may include an anchor at an end of the gripping stand that is opposite the vertex. The anchor may be any appropriate tip shape, such as a barbed, mushroom-shaped/dome-shaped, hook-shaped, ball-shaped, T-shaped, etc. For example, in some variations the anchor comprises a knob shape (e.g., a ball or flattened ball shape).

The plurality of gripping strands may comprise a plurality of V-shaped griping strands. For example, the gripping strands may include a pair of projecting posts that extend from the second (e.g., top) surface of the implant, e.g., the substrate. In some variations the plurality of gripping arms comprises a plurality of single gripping arms extending from each vertex and connected by a length of filament extending along the second side of the ECM to an adjacent gripping arm. In some variations a mixture of double (e.g., 2 gripping strands) and single gripping strands are included.

Each arm of each gripping stand may be configured to be tilted relative to the second side of the substrate; for example, the tilt angle (also referred to herein as the post angle) may be between about 85 and about 50 degrees (e.g., between 85 and 55, between 85 and 60, between 85 and 65, between 85 and 70, between 75 and 50, between 80 and 50, between 70 and 50, between 65 and 50, between 60 and 75, etc.).

In any of the apparatuses (e.g., implants) and methods described herein may include gripping strands that extend proud of the substrate by a length of, e.g., between about 4 mm and 0.01 mm (e.g., between about 3 mm and about 0.1 mm, between about 2.5 mm and about 0.5 mm, between about 3 mm and about 1 mm, between about 3 mm and about 1.25 mm, between about 2.5 mm and about 1.5 mm, between about 4 mm and about 2 mm, between about 3 mm and about 2 mm, between about 2 mm and about 0.5 mm, between about 2.75 mm and about 2 mm, between about 1.5 and about 0.5 mm, etc.).

Any of the implants described herein may have a density of gripping strands extending proud of the second side (e.g., top) of the substrate that is between about 5-50 gripping strands per $cm^2$, between about 15-25 post/$cm^2$, between about 10-40 gripping strands per $cm^2$, between about 8-30 gripping strands per $cm^2$, between about 20-35 gripping strands per $cm^2$, between about 20-50 gripping strands per $cm^2$, etc.

As mentioned, the gripping strands may be formed of a resorbable material. In some variations the first stand of material (e.g., the continuous first stand) to which the plurality of gripping strands extend may be a resorbable material. In some variations, the continuous second strand of material may be formed of a non-resorbable material.

In general, the apparatuses (e.g., implants) described herein may include both the plurality of gripping strands coupled on the back (first) side of the implant to a first strand of material, and a stitched pattern that modifies the compliance (e.g., a grid pattern such as a compliance control pattern, including but not limited to a corner lock stitch pattern). In some variations the stitched pattern (e.g., the grid pattern) and the stitching forming the plurality of gripping strands (including the first strand) align or overlap. For example, the gripping strands may extend from the substrate at vertex that is shared with a vertex of the stitching pattern; the vertex of the stitching pattern is a point through the substrate that the stitch passes (e.g., so that the upper and lower filaments forming the stitching pattern may engage with each other). Alternatively, in some variations the stitched pattern (e.g., the grid pattern) and the stitching forming the plurality of gripping strands (including the first strand) do not align, so that the vertices of the gripping strands is offset from the vertices of the stitched pattern, including in some variations approximately equidistant between adjacent vertices of the stitched pattern.

As mentioned, the first strand to which the plurality of gripping stands are attached (e.g., wrapped around) at their vertices, may be arranged adjacent to the first (e.g., back) side of the substrate in a back-and-forth pattern. This back-and-forth pattern refers to the use of a continuous strand that is sewn along the back of the implant so as to form the distribution of the gripping strands. In some variations the back-and-forth pattern may refer to a raster pattern that extends over the length of the substrate. The back-and-forth pattern may refer to a pattern that sinusoidal and/or linear. The back-and-forth pattern may refer to any pattern that extends along the back of the implant in a line that covers the extent of the implant substrate. The back-and-forth pattern may extend from the left to right, top-to-bottom, or from the top-to-bottom, left-to-right. In some variations the back-and-forth may extend in a spiral pattern, e.g., from the center of the implant outward, or outward in. In some variations, the back-and-forth pattern refers to adjacent sub-regions.

As mentioned, the substrate may be one or more sheets of ECM comprises collagen. Thus, the substrate may include a second or more sheets of ECM layered onto the first sheet of ECM and held against by the grid pattern, wherein the grid pattern is stitched through both the sheet of ECM and the second or more sheets of ECM.

The plurality of gripping strands may generally be configured so that the grip strength of the implant is greater than at least twice the gripping strength of the sheet of ECM without the plurality of gripping strands.

The grip strength may refer to the sheer strength (e.g., the force required to move the implant against another surface, such as the tissue and/or against a sheet of substrate not including gripping strands extending therefrom). Thus, the grip strength may refer to the strength when pulling two pieces across each other in opposing directions, i.e. sliding one section across the other. This may indicate the ability of the implant to resist separation when applied into the tissue. The relative sheer strength of the substrate without gripping strands compared to with gripping strands may be greater than twice (e.g., greater than 3×, greater than 5×, greater than 7.5×, greater than 10×, greater than 12×, greater than 15×, greater than 20×, greater than 30×, greater than 35×, greater than 40×, greater than 50×, greater than 75×, greater than 100×, etc.).

As mentioned above, in any of the implants described herein, the grid pattern and the plurality of gripping strands may be configured so that the implant has a peak compliance strain at a load of 16 Newtons per centimeter (N/cm) that is between 10% and 30%. For example, the orientation, dimensions, density and/or size of the grid pattern and the plurality of gripping strands may be chosen so that the peak compliance strain at a load of 16 Newtons per centimeter is between 10% and 30%.

Also described herein are methods for manufacturing any of the implants described herein, e.g., by stitching the pattern into the substrate forming the biotextile (e.g., ECM layers). In some variations, a method of making an implant having a plurality of gripping strands that enhance the gripping strength of the implant, may include: stitching a first pattern into one or more sheets of a substrate material over a mask that is positioned adjacent to a first side of the one or more sheets of the substrate material, wherein the first pattern comprises a continuous first strand of material extending adjacent to a second side of the sheet of substrate material and a second strand of material extending adjacent to the mask; and cutting the stitched second strand of material to release the mask from the one or more sheets of the substrate material and to form a plurality of gripping strands extending proud of the first side of the sheet of substrate material, wherein each gripping strand of the plurality of gripping strands comprises one or more arms extending from a vertex in which the gripping strand is wrapped around the continuous first strand of material extending adjacent to the second side of the sheet of substrate material. Any of these methods may include stitching a first compliance control pattern into the one or more sheets of substrate. For example, stitching the first compliance control pattern may comprise stitching a grid pattern, as described above. The compliance control pattern may be stitched before stitching the first pattern.

For example, described herein are methods of forming an implant comprising a plurality of gripping strands extending proud of a first side of the implant to increase the gripping strength of the first side, the method comprising: stitching a back-and-forth pattern into the one or more sheets of ECM over a mask on the first side of the ECM, wherein the back-and-forth pattern comprises a continuous first strand of material extending adjacent to a second side of the ECM and a continuous second strand of material extending adjacent to the first side of the ECM; and cutting the continuous second strand of material to remove the mask and form a plurality of gripping strands extending proud of the first side of the ECM, wherein each gripping strand of the plurality of gripping strands comprises one or more arms extending from a vertex that is wrapped around the continuous first strand of material extending on the second side of the ECM.

For example, a method of making an implant comprising a plurality of gripping strands extending proud of a first side of the implant to increase the gripping strength of the first side may include stitching a first grid pattern into one or more sheets of extracellular material (ECM); stitching a back-and-forth pattern into the one or more sheets of ECM over a mask on the first side of the ECM, wherein the second pattern comprises a continuous first strand of material extending adjacent to a second side of the ECM and a continuous second strand of material extending adjacent to the first side of the ECM; cutting the continuous second strand of material to remove the mask and form a plurality of gripping strands extending proud of the first side of the ECM, wherein each gripping strand of the plurality of gripping strands comprises one or more arms extending from a vertex that is wrapped around the continuous first strand of material extending on the second side of the ECM; and forming an anchor at an end of each arm opposite from the vertex.

Thus, any of these methods may include stitching a first a compliance control pattern, e.g., a grid pattern (such as but not limited to a corner lock stitch pattern), into one or more sheets of extracellular material (ECM). This stitching pattern may be stitched before stitching the first strand and the strand that will form the plurality of gripping strands.

Any of these methods may also include forming an anchor at an end of each arm opposite from the vertex. For example the anchor may be formed by heating the end of each arm. In some variations the anchor is formed when cutting the continuous second strand of material for example, the continuous second strand of material may be cut by heating, e.g., heating the mask. The anchor(s) may be formed into any appropriate shape, e.g., a knob-shape, at the end of each arm.

The mask may be any appropriate mask. For example, the mask may be a mesh (e.g., a wire mesh), wire grid, sieve, perforated sheet, perforated plate, etc. the mask is typically applied to the top side of the substrate and sewn over, and may then protect the substrate as the filament on the top side of the substrate is cut to form the plurality of gripping strands. As mentioned above, the first grid pattern, e.g., compliance control pattern, may be stitched into the substrate before the stitching pattern used to form the plurality of gripping strands. Alternatively, the first grid pattern may be stitched after cutting the continuous second strand.

In some variations the method may include cutting the continuous second strand so that the plurality of gripping strands comprise a plurality of V-shaped griping strands.

It should be noted that the term "continuous" strand may refer to a strand that is continuous over a portion of the implant, but does not require that the strand be continuous over the entire surface. A continuous strand may refer to a single line of stitching that is continuous; the line of stitching may include multiple pieces of filament (e.g., threads) that are follow each other in the stitching pattern.

The method described herein may include cutting the continuous second strand so that each arm of each gripping stand comprises a tilt angle relative to the second side of the ECM that is between about 85 and about 50 degrees, as mentioned above (or any sub-region within this range).

The method described herein may include cutting the continuous second strand so that each arm of each gripping stand is between 3 mm and 0.1 mm long, as mentioned above (or any sub-region within this range, such as between about 2.5 mm and 1.5 mm).

The method described herein may include cutting the continuous second strand so that density of gripping strands extending proud of the second side of the ECM of between about 5-60 gripping strands per $cm^2$, as mentioned above (or any sub-region within this range, such as about 8-30 gripping strands per $cm^2$).

Also described herein are methods of using any of the implants described herein, including using any of these implants for tissue repair, such as (but not limited to) hernia repair). For example, described herein are methods of repairing a tissue including applying an implant having a plurality of gripping strands extending proud of a top side of the implant onto a first tissue, and attaching a second tissue against the tip side so that the plurality of gripping strands engage with (and grip) the second tissue, preventing it from sliding off of the implant. The tissues may then be sutured to the implant, and the patient allowed to heal. The implant may further provide the compliance properties described herein; for example, the implant may have a peak compliance strain at a load of 16 Newtons per centimeter (N/cm) that is between 10% and 30%. In some variations the gripping strands may preferentially be resorbed by the body (e.g., leaving the implant, including the substrate and/or the grid pattern).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 10A is an example of another prototype sewn gripping surface having a dual stitched pattern.

FIG. 10B shows an enlarged view of a region of the device of FIG. 10A.

FIGS. 12A-12B illustrate an example of an implant material as described herein. FIG. 12A shows an illustration of a front of the implant material and FIG. 12B shows an example of a back of the implant material.

FIGS. 13A-13B illustrate an example of an implant material as described herein. FIG. 13A shows an illustration of a front of the implant material and FIG. 13B shows an example of a back of the implant material.

FIGS. 14A-14B illustrate an example of an implant material as described herein. FIG. 14A shows an illustration of a front of the implant material and FIG. 14B shows an example of a back of the implant material.

FIGS. 15A-15B illustrate an example of an implant material as described herein. FIG. 15A shows an illustration of a front of the implant material and FIG. 15B shows an example of a back of the implant material.

DETAILED DESCRIPTION

Figure 1A:
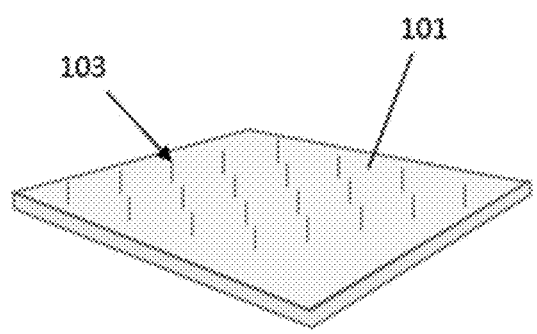
FIG. 1A shows a first example of a material having a sewn texture surface, the material including a base (substrate) formed of a biotextile/medical textile, such as a collagen material. A relatively low density of gripping strands (e.g., projections) per unit area are stitched into the surface of the material.

Described herein are implants including medical textiles (e.g., biotextiles), that include a substrate into which stitching material (e.g., filament, collection of filaments, etc.) are sewn and formed into a pattern of gripping strands (e.g., projections, loops, tufts, etc.) that extend from the surface of the medical textile/biotextile. Implant may also include one or more compliance control patterns stitched into the substrate. The gripping strands may increase the grip strength of the implant.

Any of the implants (e.g., medical textiles/biotextiles) described herein may be configured as a surgical implant structure, or may be included as a surgical implant material. For example, any of these medical textiles/biotextiles may be configured as a surgical repair graft devices. A surgical repair graft as described herein may be useful for supporting or repairing a body tissue such as for breast reconstruction, hernia repair, pelvic organ prolapse treatment, and so forth. In some examples it may be implanted. In some embodiments, the surgical repair graft includes one layer or a plurality of stacked layers (e.g., a plurality of stacked biotextile layers.

In general, the materials described herein are sewn (e.g., on a sewing machine) to create a surface texture that has enhanced gripping. The surface material may be formed of open or closed loops, and may be formed of or with a lock stitch (e.g., formed from 2 or more strands, e.g., filaments, threads system). In some variations one or more (e.g., 2) strands may be stitched into a continuous pattern to form a plurality of projection over the surface of the biotextile/medical textile. The materials described herein may also create texture by inserting single elements (e.g., rivet like) stitched into the biotextile or medical textile to form the gripping strands (e.g., projections). The strand may be a single filament or a bundle of filaments.

As mentioned above, any of the materials described herein may include the sewn gripping surface on a material that is also stitched with a compliance control stitch pattern that is also sewn or embroidered into the substrate of the biotextile or medical textile, which may further impart reinforcing strength, and stretch resistance and control into such substrates in addition to the an enhanced gripping from the sewn gripping surface. A biotextile or medical textile (which may be referred to as a scaffold) is typically used for soft tissue repair or reconstruction and, in this capacity, may be generally surgically implanted within the body. Such scaffolds may serve, for example, to replace or reinforce diseased or damaged soft tissue, or to hold internal organs in place in the case of a hernia repair. In some cases, these scaffolds are intended to be a permanent fixture within the body, for example, medical textile scaffolds comprising polymeric threads. In other cases, these scaffolds are intended to be a temporary fixture within the body such that they are made of a material that is gradually resorbed by the body as it is replaced by the body's own tissue, for example, biotextile scaffolds comprising an extracellular matrix. Regardless, patients do not all heal at the same rate, owing to the particular condition in need of repair, and the physical characteristics and conditions of the patient. Accordingly, it is desirable to control the inherent base properties of such scaffolds to accommodate the conditions of individual patients. In addition, it is desirable to compensate for premature breakdown or resorption of the scaffold.

Whether biologic/natural (e.g., biotextiles) or synthetic (e.g., medical textiles), implantable scaffolds have certain inherent strength and stretch properties, based on the particular material from which the scaffold is made as well as how the scaffold was made—e.g., whether assembled with layers, has any added support structures, etc. Over time, particularly after being subject to biomechanical load forces and after being exposed to a patient's immune system, and other natural factors that cannot be controlled, the scaffolds may degrade, weaken, become too elastic, or otherwise lose their original strength and stretch properties, such that the patient is put at risk. Accordingly, the negative conditions from scaffold wear and tear may be mitigated with specially designed stitching or embroidery patterns placed about the scaffold. Such specially designed patterns include compliance control stitching patterns as described and exemplified herein.

The biotextile/medical textiles described herein may include, e.g., as the substrate, biologic/extra cellular membranes (ECM's) and/or polymer substrates/base materials. A biotextile and/or medical textile may be used to form the base of any of the material having a sewn gripping surface as described herein.

In general, the sewn texture surface may: create a self-sticking property of base material to implant location, i.e. place invention to location of choice, touch to surface, implant will stick to surface, and may make sewing or tacking a fixed implant easy (enhancing anchoring). In some variations the sewn texture surface may hold an implant open/unfurled, e.g., when applying. For example, in some variations an implant material including a sewn texture surface can be slipped through small trocars in a rolled form, once unrolled, implant tend to want to roll back up (window shade), sticky textured surface (Velcro like) will stability unfurled implant). A sewn texture surface may create a self-anchoring implant. For example, the gripping strands (e.g., projections) may provide a texture that may increase shear resistance. Thus, an implant may resist migration and potentially offload the hernia closure in a manner comparable to use with an adhesive material, which may help repair (e.g., patch) tissue.

Figure 1B:
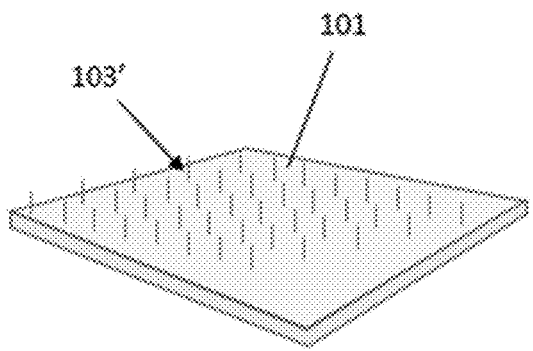
FIG. 1B shows another example of a sewn gripping surface on a base (substrate) formed of a biotextile/medical textile, such as a collagen material. A higher density of gripping strands (e.g., projections) per unit area are stitched into the surface of the material.
Figure 1C:
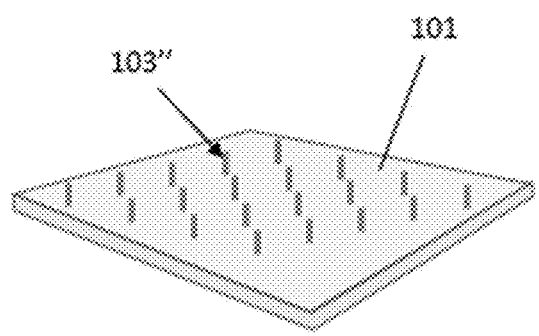
FIG. 1C shows another example of a sewn gripping surface on a base (substrate) formed of a biotextile/medical textile, such as a collagen material. Large diameter gripping strands (e.g., projections) are stitched into the surface of the material.
Figure 1D:
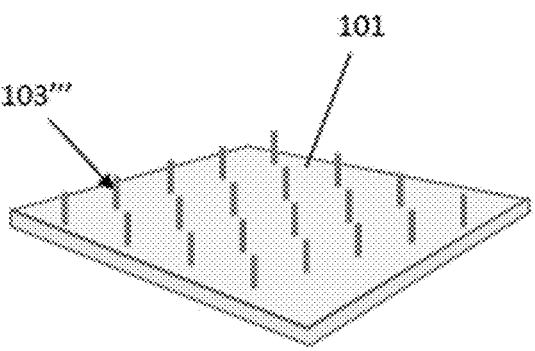
FIG. 1D shows another example of a sewn gripping surface on a base (substrate) formed of a biotextile/medical textile, such as a collagen material. Large diameter, taller gripping strands (e.g., projections) are stitched into the surface of the material.

The sewn gripping strands may form a texture that can be low or high density, e.g., in projections per unit area or stitch per length. See, e.g., FIGS. 1A-1D. FIG. 1A shows an implant having a substrate 101 with a plurality of lower density gripping strands (e.g., projections) 103. FIG. 1B shows a substrate 101' with a higher density of gripping strands (e.g., projections) 103'. In general, the texture elements (e.g., gripping strands) can be soft or stiff. The gripping strands may be formed of a polymeric material. The strand material forming the projections may be a mono filament or a multi-strand filament. For example, the material may be a monofilament having a thread diameter that is small (and typically softer, less still) or larger diameter, typically more stiff. As shown in FIGS. 1C and 1D, the filament and therefore the projections may have different heights, which may produce different shear resistances. For example the texture element may have a height that is relatively shorter is stiffer (e.g., formed of a larger diameter material) or the same material (larger diameter material) may be taller. In FIG. 1C the implant includes a substrate 101, from which a plurality of larger-diameter gripping strands 103" project. In FIG. 1D, the larger-diameter gripping strands 103''' extend taller (e.g., further from the substrate 101) than those in FIG. 1C.

In general, the gripping strands forming the sewn texture surface may have any shape at the tip (e.g., the end furthest from the substrate); this tip may form an anchor. The texture element tip (projection tip or anchor) shape may change or modify the properties of the sewn texture surface. For example, a gripping strand having a blunt tip may resist shear. Gripping strands having pointy tips may engage tissue, and may resist shear. Gripping strands having barbed tips may engage tissue, stick, and may help resist shear. Gripping strands having t-shaped anchors may resist shear, and may help the sewn texture surface stick to an adjacent material (including tissue). As shown below in FIGS. 6-9, gripping strands having a mushroom or domed shape may allow the sewn texture surface to resist shear and/or stick. Gripping strands having a hook shape may engage tissue, stick, and help the sewn texture surface resist shear. Loop-shaped (e.g., closed loop projections) may help the sewn texture surface resist shear, and may improve long term anchoring/resistance to migration.

Figure 2A:
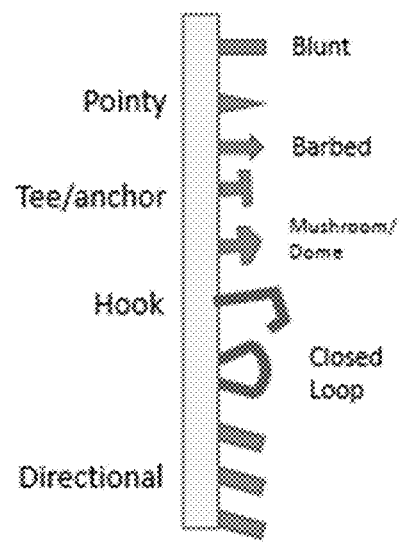
FIG. 2A shows a variety of gripping strands (e.g., projections) anchor shapes and orientations that may be used to form a sewn gripping surface/material.
Figure 2B:
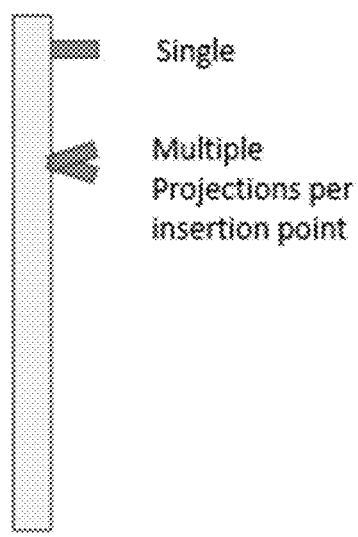
FIG. 2B shows examples of single and multiple gripping strands (e.g., projections) per insertion point that may be used to form a sewn gripping surface/material.

Any of the sewn texture surface may include projections (or groups of projections) that are directional. Directional projections may also help the sewn texture surface resist shear directionally. Many of the examples of projections are illustrated in FIG. 2A. In general, any of the sewn texture surfaces described herein may include a distribution of single projections or multiple (2 or more, e.g., 3, 4, 5, etc., including tufts) projections per point (single versus multiple), as shown in FIG. 2B.

Any appropriate material may be used for the strand (e.g., filament) including polymeric materials and non-polymeric materials. The strand may be sewn in the shape of the texture element. For example, the strand may be a monofilament or a plurality of filaments. Examples of strands formed of a polymer may include a permanent polymer (e.g., PET, Polypro, Nylon, PTFE, metals, etc.). Other permanent materials (metals, organic materials, etc.) may be used. The strand forming the sewn texture surface may also or alternatively be formed of a biodegradable material such as, e.g., PGA, PLLA, PDO, co-polymers of these, P4HB, Silk, etc. In some variations the sewn texture surface is sewn with a mixture of permanent and biodegradable polymers forming the projections.

Any of the sewn texture surfaces and/or the strand(s) forming them may be coated (e.g., antibiotics, anti-inflammatory), impregnated, or the like. Any of the sewn texture surface may include (including as the strand or part of the strand forming the sewn texture surface projections) a radiopaque material such as, but not limited to, barium doped or metallic (gold, Pt, Pt Iridium, etc.).

For example, in some variations the sewn texture surface is formed by sewing a strand of monofilament, e.g., 0.003" to 0.011" (non-closed loop designs). In some variations the sewn texture surface is formed by sewing a strands of a multifilament: 20 D to 3000 D (closed loop designs).

Figure 3A:
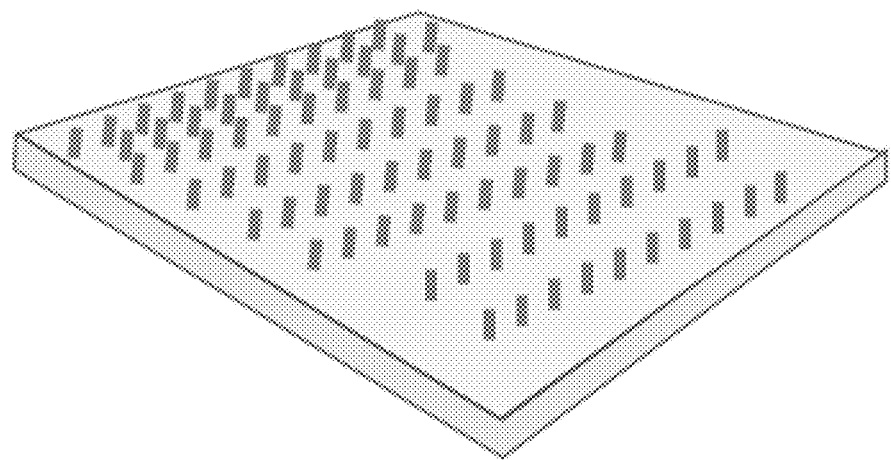
FIG. 3A is an example of a sewn gripping surface having a gradient of gripping strands (e.g., projections).
Figure 3B:
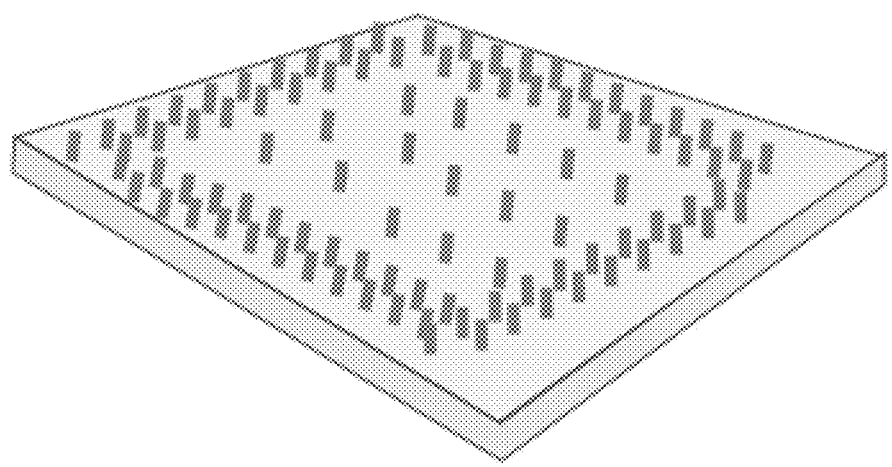
FIG. 3B is an example of a sewn gripping surface having a framing region of gripping strands (e.g., projections).

Any pattern of projections may be used to form the sewn texture surface. FIGS. 3A-3B illustrate just two: a textured surface gradient (FIG. 3A) and a textured surface having a frame region formed of filaments. These designs may provide different adhesive/sliding resistance properties. For example, the gradient may increase the resistance to sticking/sliding along the surface as it transitions from lower-density to higher density regions.

Figure 4:
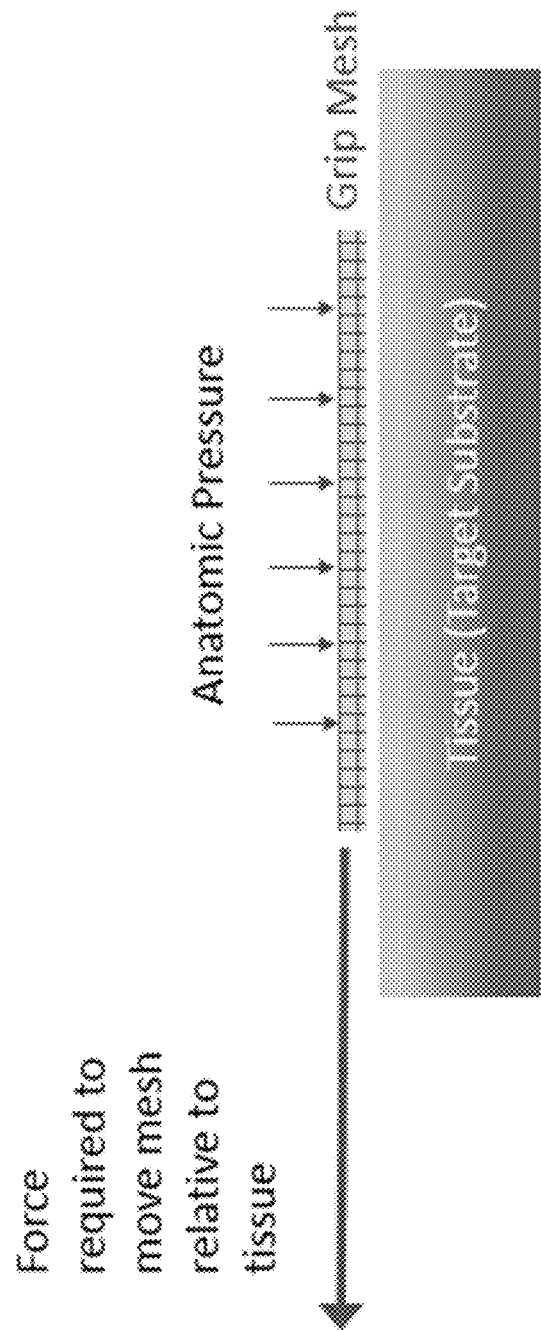
FIG. 4 is an example of an experimental set-up showing the measurement of grip force; this set up may be used to examine the grip force of the materials, e.g., sewn gripping materials, described herein.

In general, the force required to move mesh relative to tissue in the surface may be measured. For example, FIG. 4 illustrates one example of a setup to measure the shear force to move a material such as the sewn texture surface on the tissue. Depending on the density, distribution and shape of the projections in the sewn texture surface, the force required (gripping force) may be from 1.2× to 100× (or more) the force required to move the same substrate material with the sewn texture surface (e.g., between 1.5× to 90×, between 1.5× to 80×, between 2× to 70×, between 2× to 60×, between 1.5× to 50×, etc. or greater than 3×, 4×, 5×, 7.5×, 10×, 20×, 50×, 70×, 100×, 150×, 200×, etc.). The grip force may be measured as shown in FIG. 4 as the force required to move the material relative to the tissue.

Figure 5:
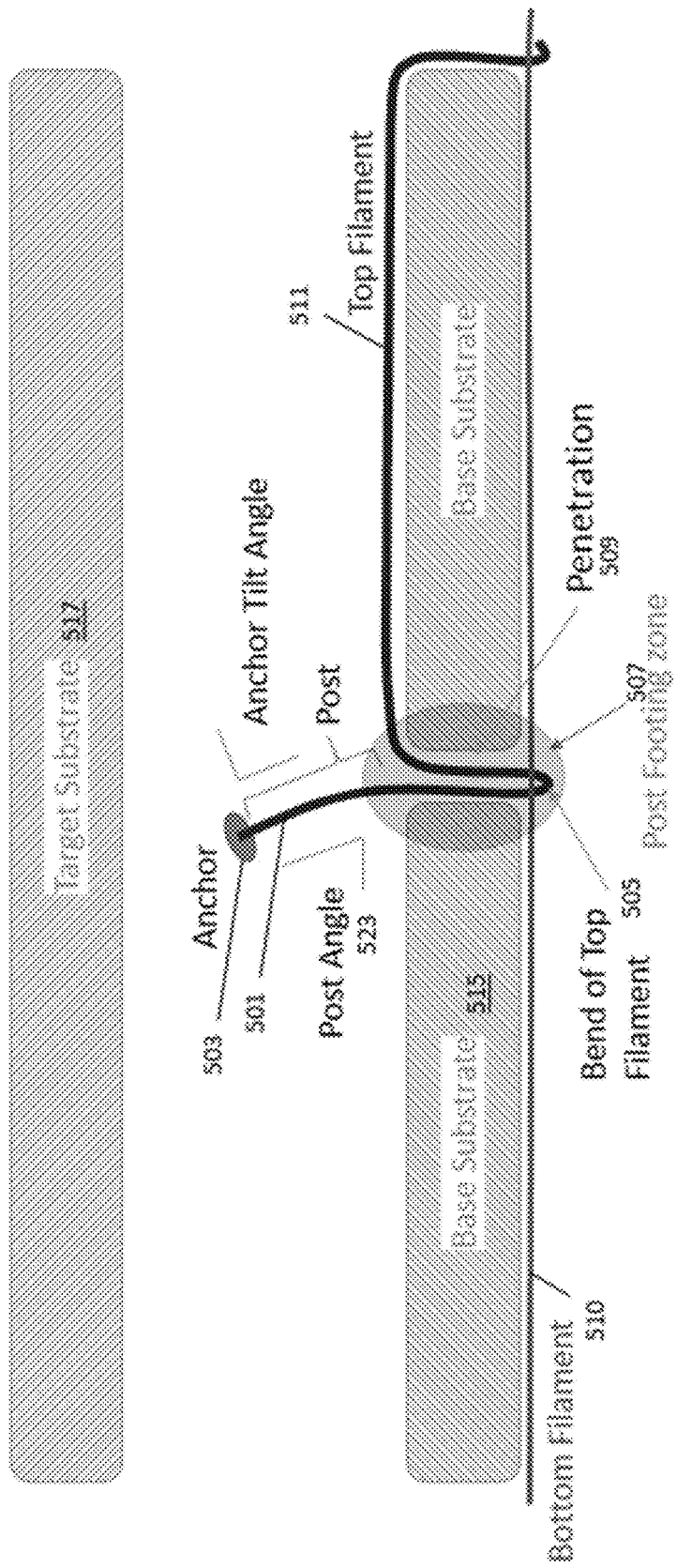
FIG. 5 illustrates one example of a region of a sewn gripping surface, illustrating some of the components that may be included.

FIGS. 5-8 illustrate examples of sewn texture surfaces having gripping strands as described herein. In FIG. 5 the sewn texture surface includes a single gripping strand 501 having an anchor 503 at the distal end. The gripping strand has a tilt angle 523 (e.g., between 90 degrees and 30 degrees, between 85 degrees and 45 degrees, between 85 degrees and 50 degrees, etc., between an upper angle of: 89, 88, 87, 86, 85, 84, 83, 82, 81, 80, 79, 78, 77, 76, 75, 74, 73, 72, 71, 70, etc., and a lower angle of: 20, 25, 30, 35, 40, 45, 50, 55, 60, 65, etc.). The gripping strands is sewn into the base substrate and may interact with the target substrate (e.g., tissue, another material, implant, etc.). The gripping strand 501 is sewn from a top strand (e.g., top filament 511) that is engaged with a bottom strand (e.g., bottom filament 510) on the other side of the substrate. The gripping strand bends 505 around the bottom strand 510. The connection of the gripping strand to the bottom filament may flexibly and movably secure the gripping strand(s) in position on the substrate, to that the gripping strand is able to move and flex without pulling on the substrate, or by distributing the pulling force over the back of the implant because of the distribution of the continuous second strand (bottom filament) that extends along the back of the substrate 515.

The gripping strand example shown in FIG. 5 is just a single, e.g., zoomed-in, example of one gripping strand. Multiple gripping strands may be included an each may twist around the bottom strand 510 a vertex 507 (e.g., footing zone). The bottom filament 510 may continue in a pattern adjacent (e.g., immediately adjacent) to the substrate 515 that may include one or more layers of substrate material (e.g., ECM). The gripping strand 501 may pass thorough the substrate at a penetration site at the vertex 509. As will be described later, this vertex/penetration site may be shared with a penetration site for stitching a compliance control pattern (not shown in FIG. 5) to the substrate. The implant, via the plurality of gripping strands, may engage directly with the target 517, which may be, e.g., tissue or another implant.

Figure 6:
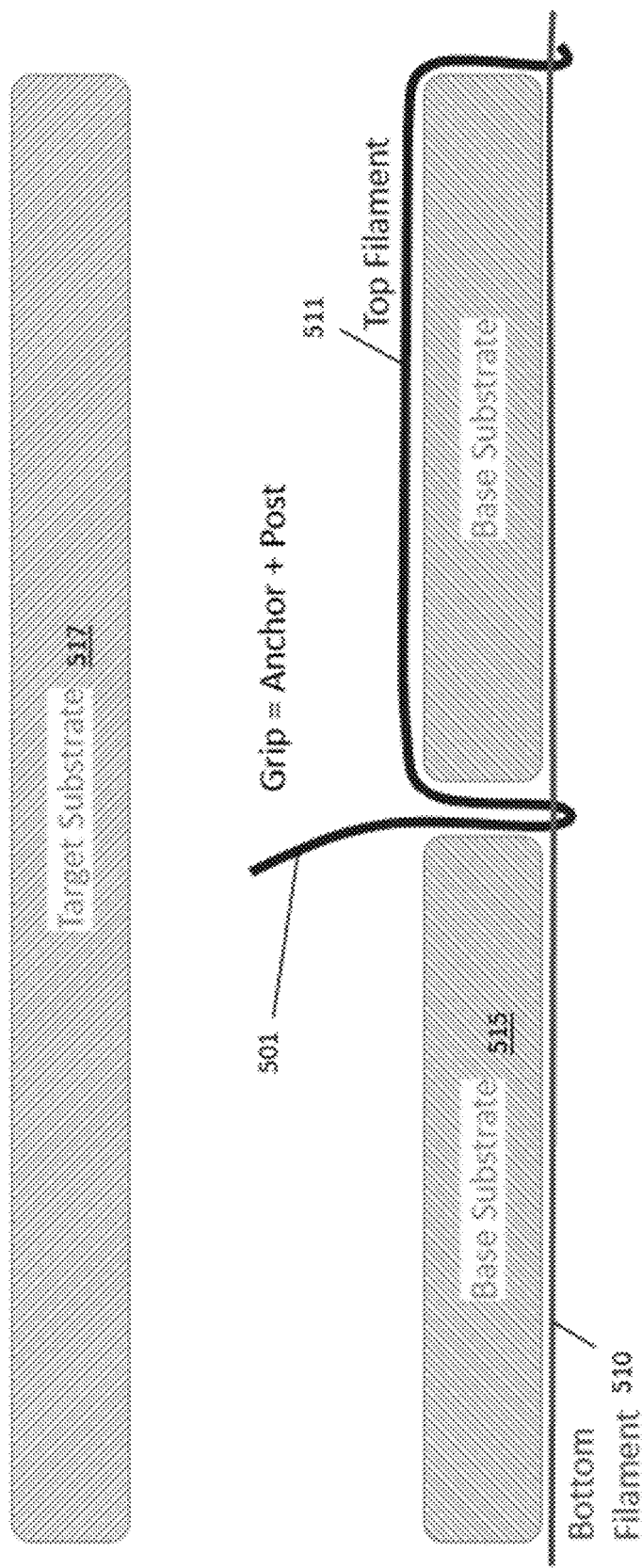
FIG. 6 illustrates another example of a region of a sewn gripping surface, illustrating some of the components that may be included.

FIG. 6 shows a similar configuration, with the top filament 511 forming a bend under the base substrate 515; a single projection is again shown. In this example the end of the gripping strand 501 does not include an anchor structure.

Figure 7:
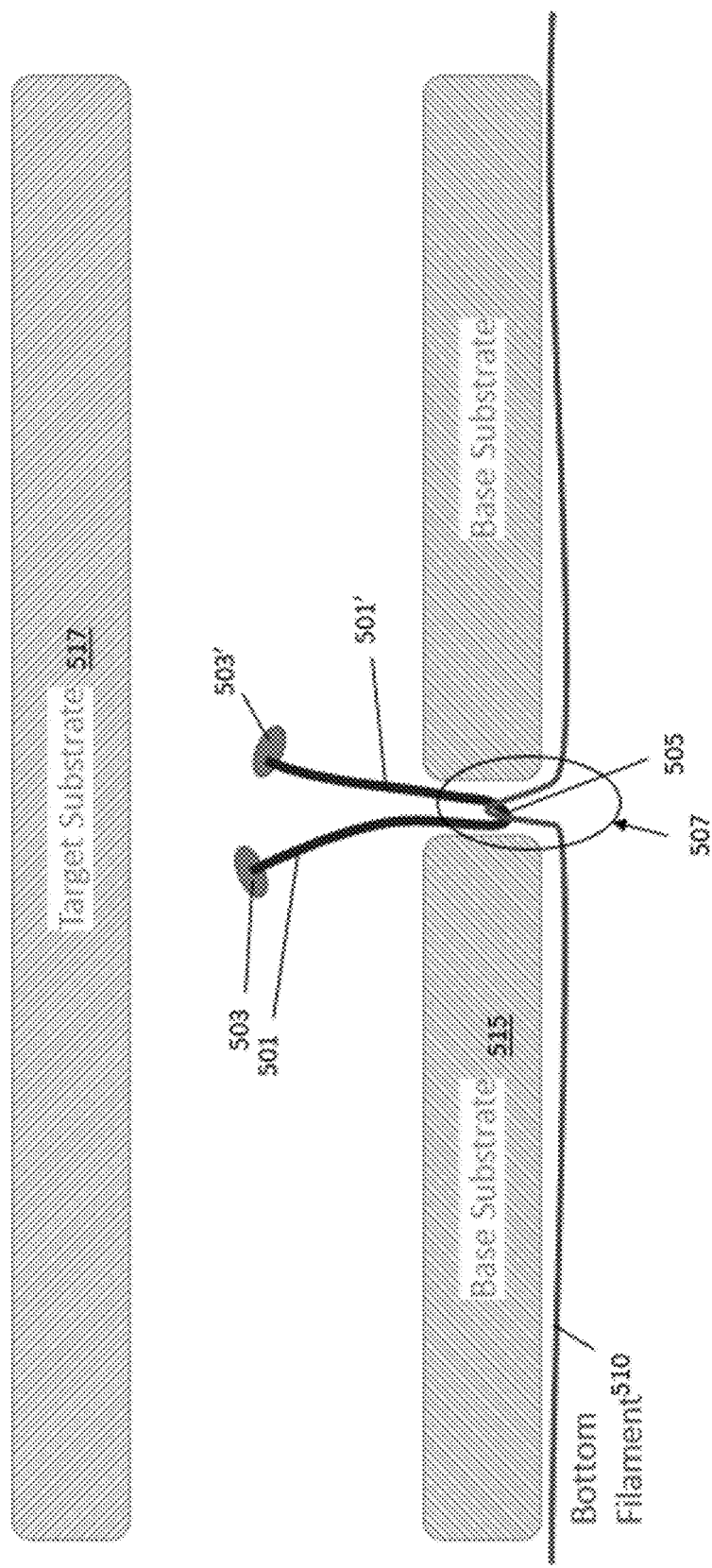
FIG. 7 illustrates another example of a region of a sewn gripping surface, illustrating some of the components that may be included.

In FIG. 7, a pair of gripping strands 501, 501' are shown formed from the top filament. The two gripping strands each include an anchor at their distal ends. The strands are connected at a vertex 507 the bottom strand 510 (bottom filament) similar to that shown in FIGS. 5-6, where the pair of gripping strands are bent 505 around this bottom strand.

Figure 8:
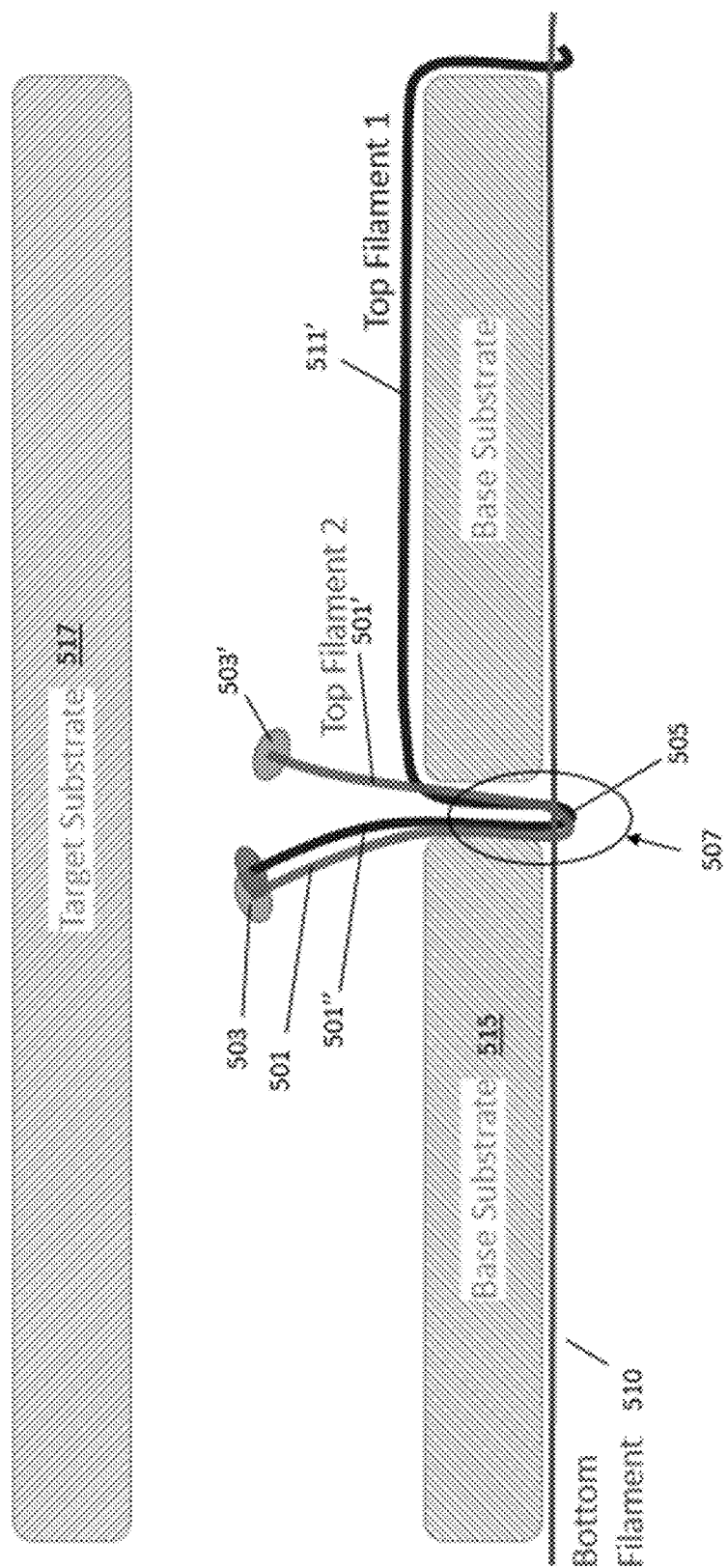
FIG. 8 illustrates another example of a region of a sewn gripping surface, illustrating some of the components that may be included.

Similarly, in FIG. 8, shows an example in which three gripping strands 501, 501', 501" are formed, e.g., by stitching a second top filament 511' (in addition to the first filament forming the first gripping strand 505 and the second gripping strand 505'), that is similarly cut to form a third gripping strand 505" sharing the same vertex 507 and warped around 505 the same bottom strand 510 on the underside of the implant, forming a tuft of projections. In some variations the tip filament may extend to an adjacent vertex and may form another gripping strand (not shown in FIG. 8). Alternatively, in some variations a fourth (or more) gripping strand may be formed by cutting the top filament.

Figure 9A:
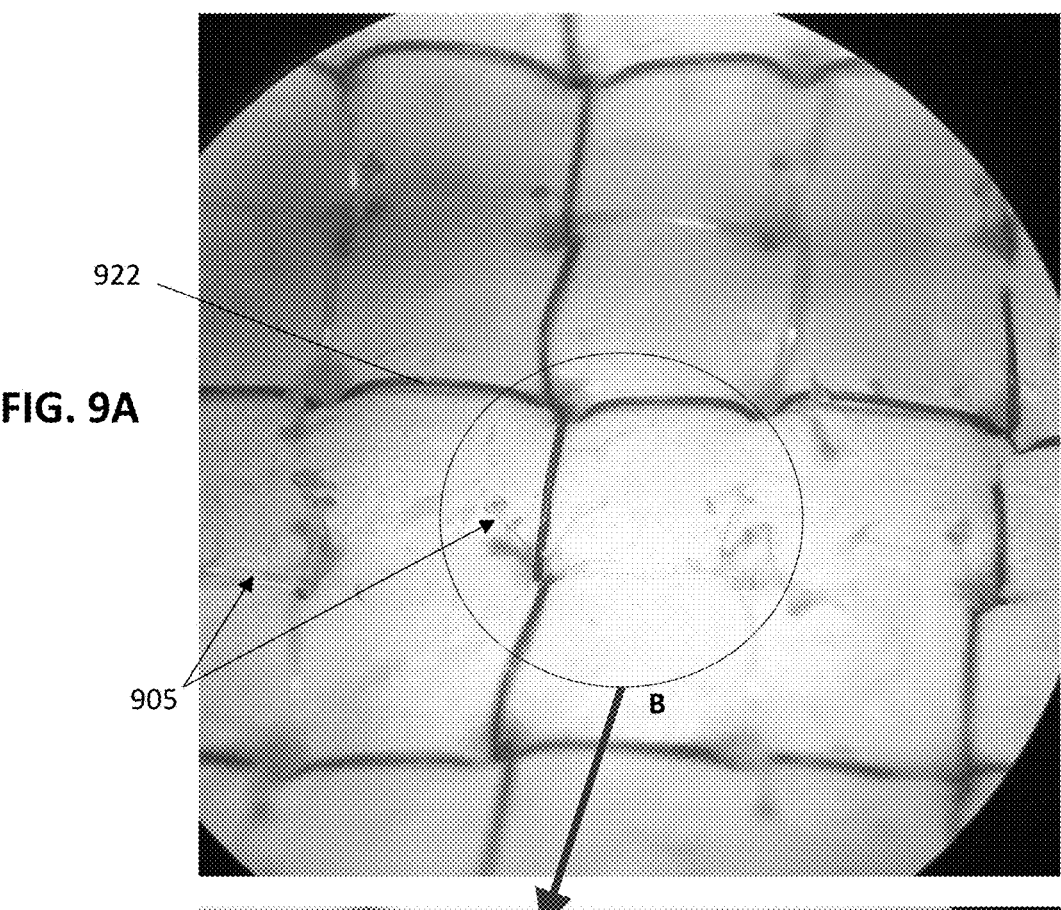
FIG. 9A is an example of a prototype sewn gripping surface, showing projections configured with enlarged (e.g., "mushroom") tops.
Figure 9B:
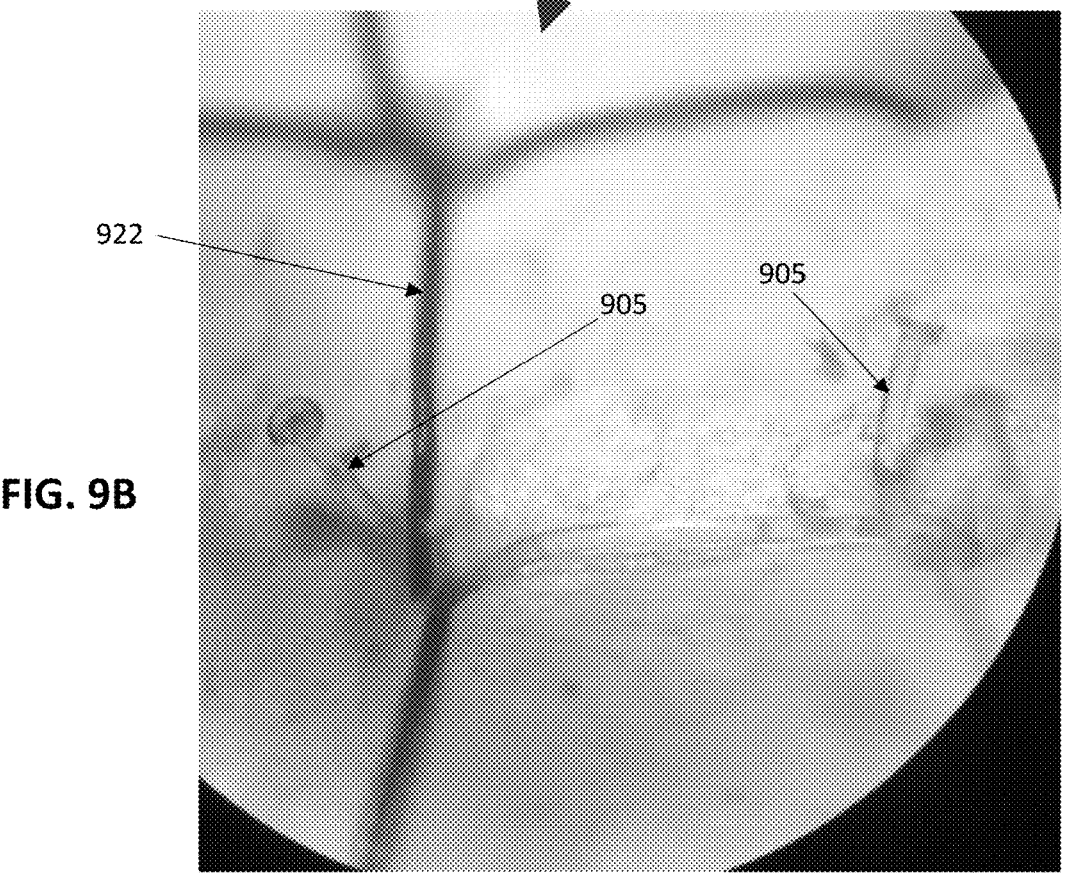
FIG. 9B is an enlarged view of the prototype sewn gripping surface of FIG. 9A.

FIGS. 9A-9B illustrate an example of a prototype sewn texture surface, having a substrate of ECM material along with a second (e.g., compliance control) stitching pattern as described herein. FIG. 9A shows the top surface including a compliance control stitching pattern 922 and a plurality of gripping strands 905. FIG. 9B shows and enlarged view of region B. In this example, the gripping strands share a vertex (needle penetration region) through the substrate with the compliance control region.

FIG. 10A is another example of a prototype of an implant as described herein, showing a top surface of a substrate (e.g., one or more layers of ECM) 1001 through which a plurality of griping strands 1005 extend proud, at an angle of between 65 degrees and 85 degrees, as shown. The ends of each gripping strand have been formed into an anchor (showing a mushroom-like head 1013). This is shown in greater detail in FIG. 10B, showing an enlarged view. In FIG. 10A the implant also includes a compliance control stitching pattern, shown as a grid stitching pattern (having parallel lines of stitches that crossover each other, as shown), similar to what is shown in FIG. 9.

Figure 11:
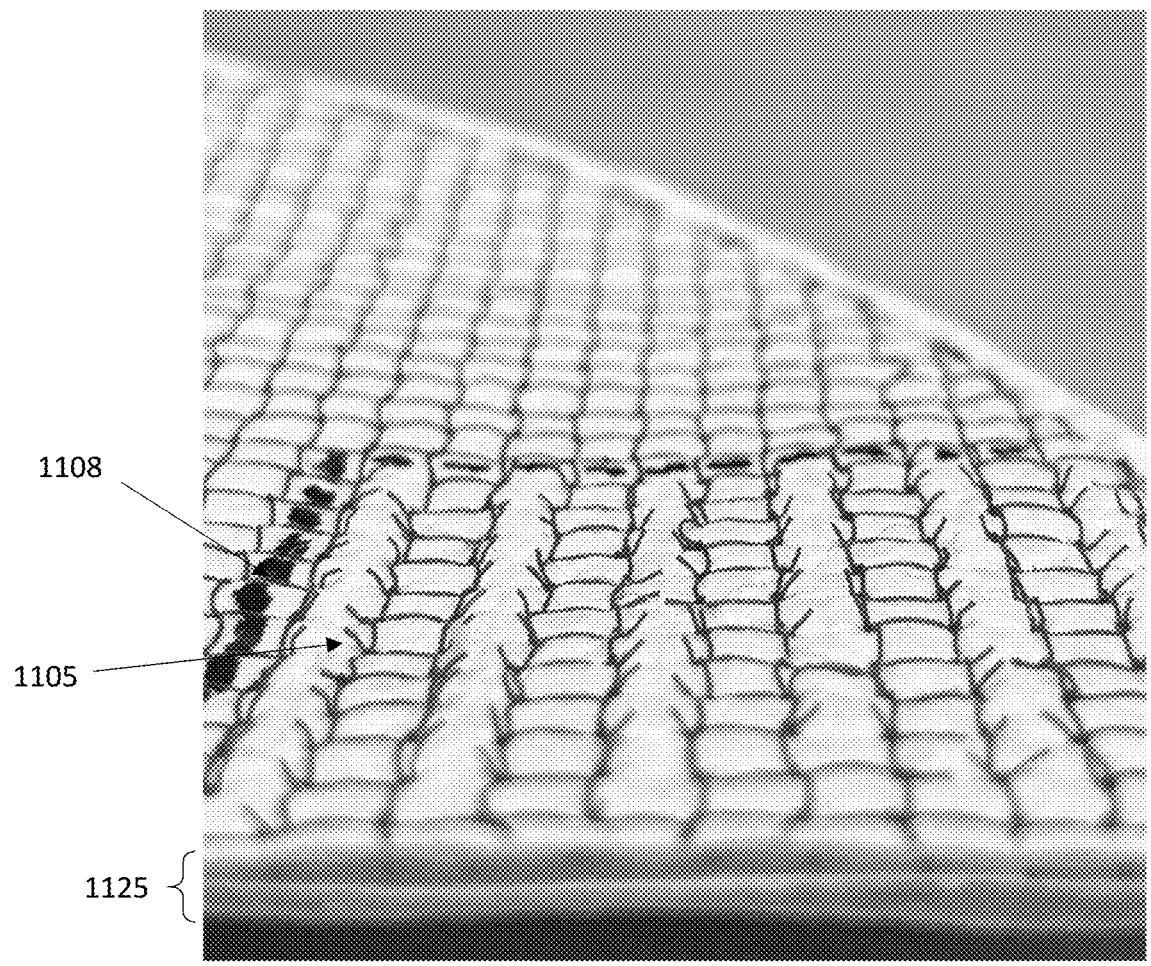
FIG. 11 is an example of a lower-grip prototype sewn gripping surface.

FIG. 11 illustrates another example of a prototype device in which a portion of the implant has been formed into a plurality of gripping strands, by first sewing to form a grid-like pattern, using a first strand on the bottom (not visible) and a second strand on the top. In FIG. 11 another stitching pattern if formed at an angle (e.g., in FIG. 11, perpendicular) to the first pattern, which may provide compliance control. A portion 1108 of the top of the implant in FIG. 11 has been processed by cutting to form a plurality of gripping strands 1105. The substrate 1125 shows a plurality of layers of ECM through which the stitching patterns have been formed. The griping strands shown do not include anchors on their ends in this example; this may provide a strong gripping force but a relatively lower peel force.

FIGS. 12A-12B illustrate another example of a portion of an implant including a plurality of gripping strands 1205 extending from the top side of the substrate 1201 of the implant. In this example pairs of gripping strands extend from the same vertex. The implant also includes a compliance control pattern 1221 that is configured as a grid pattern and more specifically as a plurality of corner-lock stitches. The corner-lock stitches comprise a first pattern of a first upper thread or yarn and a first lower thread or yarn comprising a first plurality of vertices formed from a plurality of curves, angles, or a combination of curves and angles, and a second pattern of a second upper filament and a second lower filament comprising a second plurality of vertices formed from a plurality of curves, angles, or a combination of curves and angles; wherein each vertex of the first plurality of vertices overlaps and interlocks with a vertex of the second plurality of vertices to form the plurality of corner-lock stitches. Each corner-lock stitch comprises one or more thread interlace points and two or more thread overlays in which the second upper thread and second lower thread envelope the first upper thread and first lower thread.

FIG. 12B shows the back of the implant of FIG. 12A, showing a first strand of material 1210 extending adjacent to a back side of the substrate in a pattern (e.g., a back-and-forth pattern). In FIGS. 12A-12B the gripping strands are stitched along with the first strand in a pattern that overlaps with, but is offset from, the compliance control (e.g., corner lock stitch) pattern. In contrast FIGS. 13A-13B show an example of a portion of an implant in which the gripping strands are stitched along with the first strand in a pattern that overlaps with and is aligned with the compliance control pattern.

In FIG. 13A the exemplary portion of an implant includes a plurality of gripping strands 1305 extending from the top side of the substrate 1301. Pairs of gripping strands 1305 extend from the same vertex (passing through the substrate). The implant also includes a compliance control pattern 1321 that is configured as a grid pattern and more specifically as a plurality of corner-lock stitches similar to that shown in FIG. 12A-12B. The gripping strands are shown extending from the top surface from a corner of the overlapping (locking) corner lock stitch in FIG. 13A.

FIG. 13B shows the back of the implant of FIG. 13A, showing a first strand of material 1310 extending adjacent to a back side of the substrate in a pattern (e.g., a back-and-forth pattern). The gripping strands on the front of the implant wrap around the first strand 1310 on the back side. In FIGS. 13A-13B the gripping strands are stitched along with the first strand in a pattern that overlaps and is aligned with the compliance control (e.g., corner lock stitch) pattern.

FIG. 14A is a front view of another example of an implant including a plurality of gripping strands 1405 extending proud of the substrate material 1401, overlapping with but offset from a compliance control stitching pattern 1422 that forms a grid, as shown in FIG. 14A. The compliance control stitching pattern includes overlapping patterns of stitching that decreases the peak compliance strain at a load of 16 Newtons per centimeter (N/cm) so that it is between 10% and 30%.

FIG. 14B shows the back of the implant region of FIG. 14A, showing the first strand of material 1410 extending adjacent to a back side of the substrate in a pattern (e.g., a back-and-forth pattern). The gripping strands on the front of the implant wrap around the first strand 1410 on the back side, as described above. The back of the compliance control stitching pattern 1455 is also visible in FIG. 14B. In this example, the compliance control pattern overlaps with but is offset from the stitching pattern forming the gripping strands.

FIGS. 15A-15B show an example of an implant having a compliance control pattern that overlaps and is aligned with the stitching pattern formed by the gripping strands. For example, in FIG. 15A, the top of the implant shows gripping strands 1505 sharing a vertex with the needle channels of the compliance control pattern (shown as a grid 1522 stitched through the substrate 1501). FIG. 15B shows the back side of the implant of FIG. 15A. In this example, the stitching pattern forming the gripping strands includes a continuous filament 1510 or strand that extends adjacent to the bottom surface of the implant; this continuous filament overlaps with the compliance control pattern 1522, as shown.

Figure 16A:
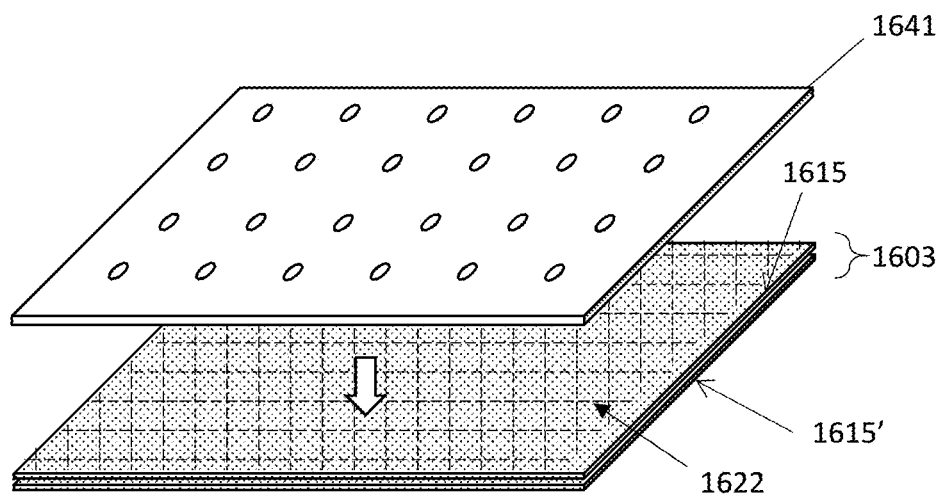
FIGS. 16A-16F illustrate one example of a method of making an implant as described herein.
Figure 16B:
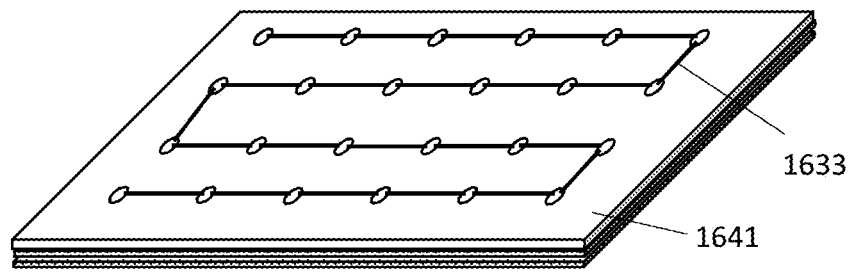

FIGS. 16A-16F illustrate the fabrication of an implant as described herein, including a plurality of gripping strands. FIG. 16A shows a view of a substrate 1603 that is formed of one or more (in this example, two) sheets of material, such as extracellular matrix material (ECM), 1615, 1615'. In this example, the substrate already includes a compliance control stitching pattern 1622 formed (e.g., stitched) thereon. A mask 1641 is placed over the top of the substrate, as shown. In FIG. 16B, a stitching pattern 1633 is passed through openings in the mask and through the substrate, so that a first strand on the bottom of the implant is wrapped by a second strand from the top of the substrate (and over the mask 1641), as shown. This stitching pattern may be formed in a back-and-forth pattern, as shown.

Figure 16C:
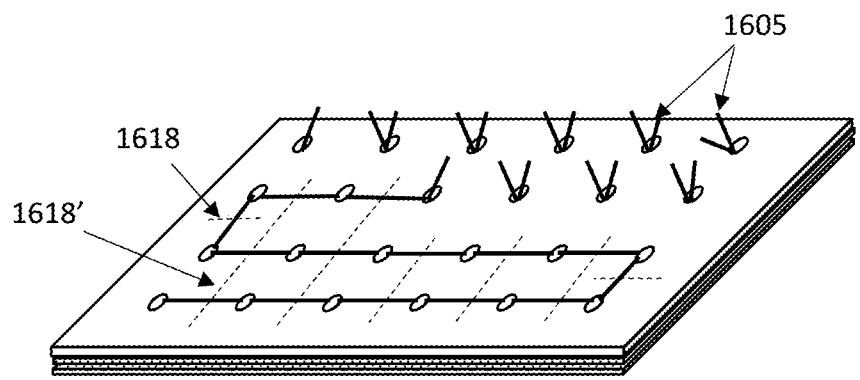

FIG. 16C illustrates the plurality of gripping strands 1605 are formed by cutting the second strand on the top, over the mask 1641. The strand may be cut as shown by the dashed lines 1618, 1618' to form the gripping strands. This cutting may be performed using a tool (e.g., die, knife, etc.) or by the application of energy (e.g., heat, electricity, etc.). The gripping strands may be processed to form one or more anchors (e.g., at the ends of the gripping strands), or to modify the angle of the gripping strands relative to the substrate.

Figure 16D:
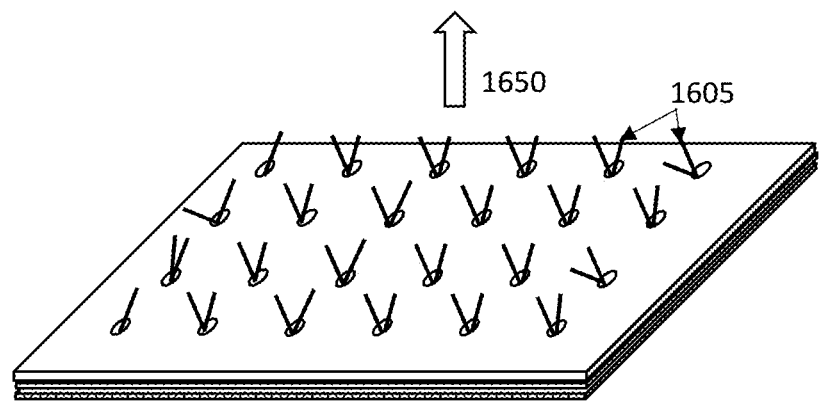
Figure 16E:
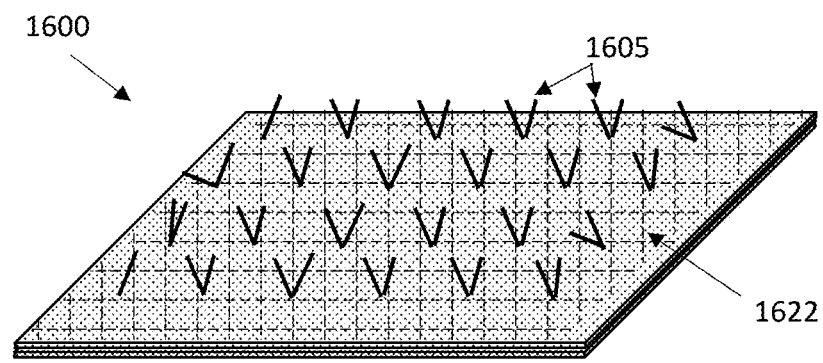
Figure 16F:
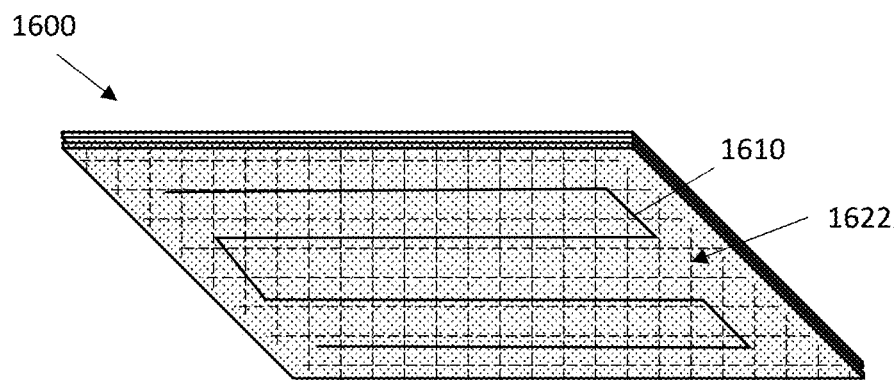

FIG. 16D shows the example of FIG. 16C with all of the second (top) strands of the gripping strand stitching pattern cut to form the gripping strands 1605. Thereafter, as indicated by the arrow 1650, the mask may be removed, showing the top surface of the implant 1600, as shown in FIG. 16E. In top of the implant shows the compliance control stitching pattern 1622 and the plurality of gripping strands 1605. The bottom of the implant is shown in FIG. 16F, showing the first strand 1610 of the stitching pattern corresponding to the gripping strand stitching pattern.

Figure 17:
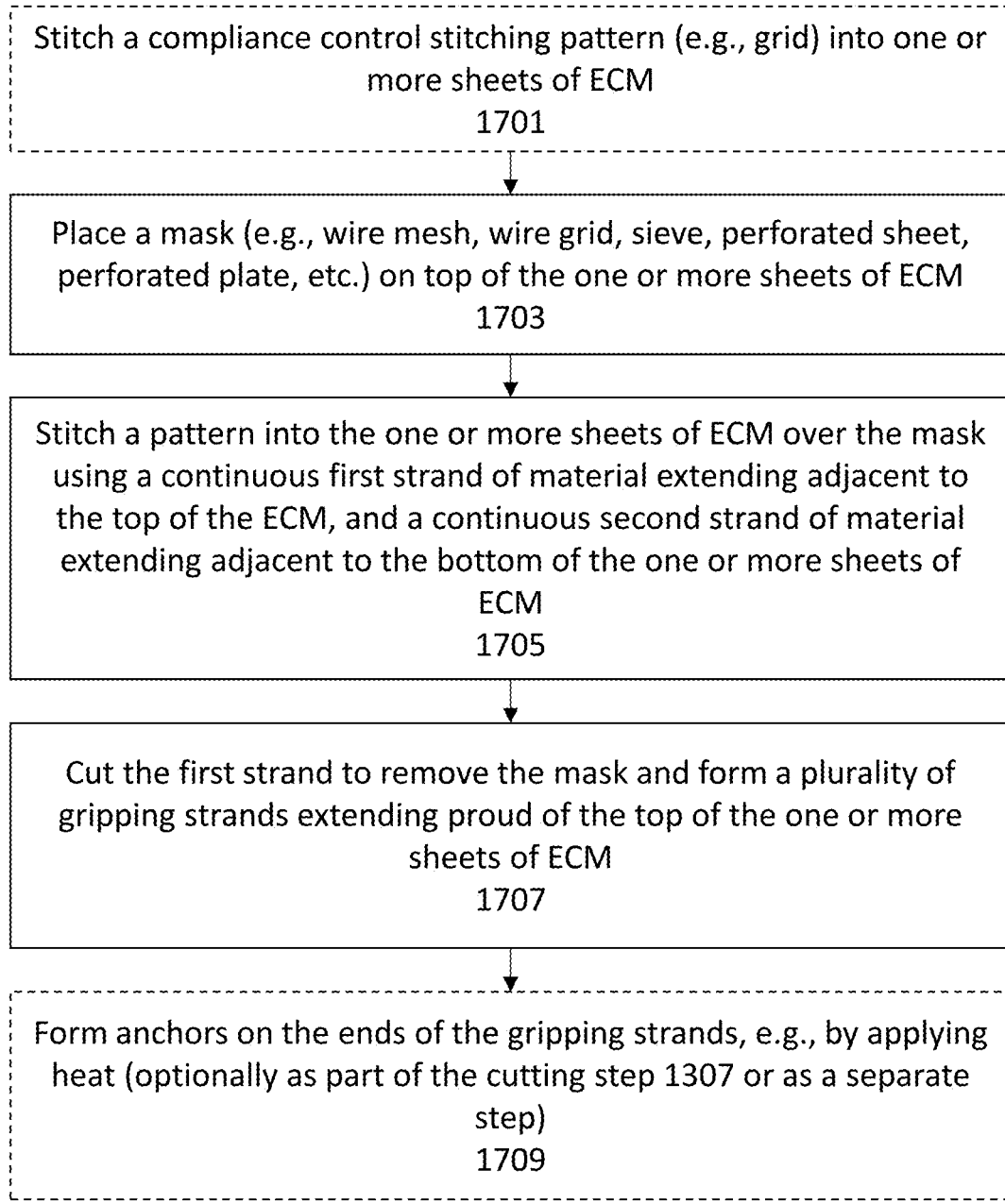
FIG. 17 schematically illustrates one example of a method of making an implant as described herein.

FIG. 17 is a flowchart illustrating a method of making an implant as described herein. In FIG. 17, the first step may optionally include stitching a compliance control stitching pattern (e.g., a grid pattern) into one or more sheets of ECM 1701. Alternatively, or additionally, a compliance control pattern may be stitched into the implant during or after forming the gripping strands.

A mask, such as a wire mesh, wire grid, sieve, perforated sheet, perforated plate, etc., may be placed on top of the one or more sheets of ECM 1703. The gripping strand stitching pattern may then be stitched into the substrate (e.g., one or more sheets of ECM) and the mask by using a continuous first strand of material extending adjacent to the top of the ECM (e.g., over the mask), and a continuous second strand of material extending adjacent to the bottom of the one or more sheets of ECM 1705.

Thereafter the mask may be removed by cutting the first strand forming the gripping strands to form a plurality of gripping strands extending proud of the top of the substrate 1707, and lifting off the mask. The first strand may be cut by any appropriate method, such as the use of a knife, die, heat, etc.

In some optional variations, anchors may be formed on the ends of the gripping strands 1709. For example, heat may be applied to form mushroom-headed ends of the gripping strands.

Figure 18:
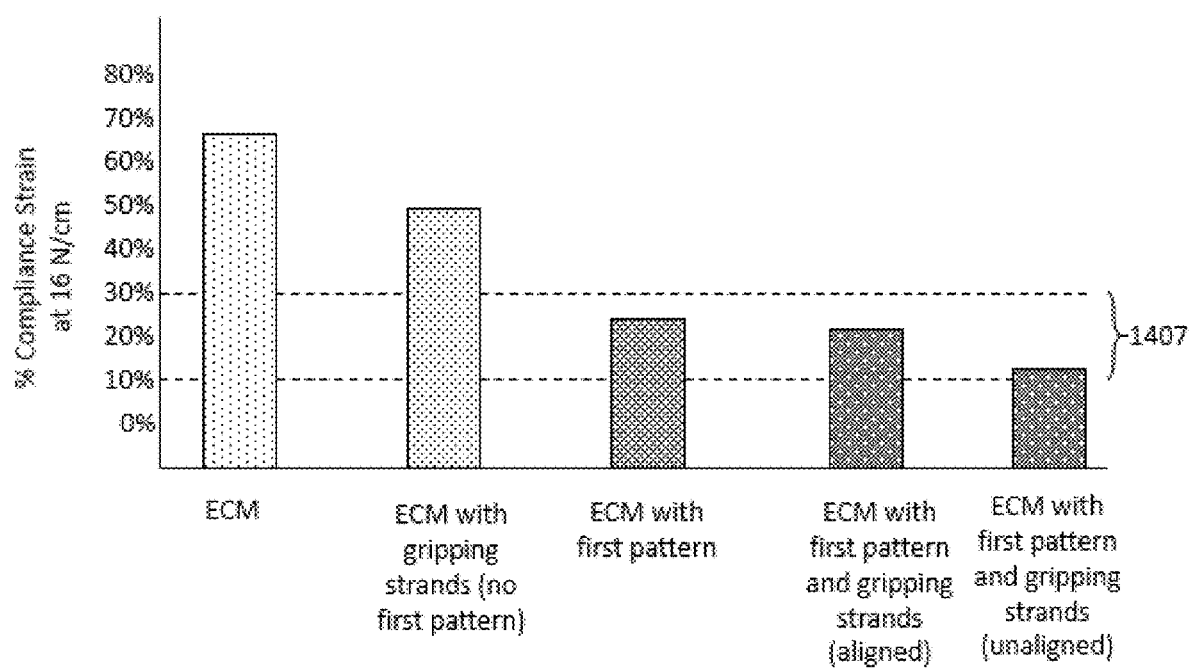
FIG. 18 is a qualitative bar graph showing the percent compliance strain at 16 N/cm, comparting ECM material, ECM material with gripping strands, ECM material having a stitching (e.g., compliance control) pattern, ECM material having the stitching pattern with gripping strands arranged in alignment with the stitching pattern, and ECM material having the stitching pattern with gripping strands arranged out of alignment with the stitching pattern. The actual percent compliance strain at 16 N/cm may depend on the density and/or number, and/or shape of the gripping strands, and the dimensions of the stitching pattern.

In any of these implants (e.g., grafts, etc.) described herein, it may be particularly beneficial to match the compliance properties of the material to the body, especially at implantation time. Over time in the body, the implant compliance may change (e.g., may increase) to prevent stiffening and discomfort due to compliance increase as the implant becomes ingrown and/or scarred. FIG. 18 illustrates the percent compliance strain at 16 N/cm of the substrate alone (far left), the substrate with the gripping strands, the substrate with a compliance control stitching pattern ("first pattern"), and either the substrate with the compliance control stitching pattern aligned with the stitching pattern forming the gripping strands or not aligned (e.g., offset). It is desirable, based on clinical and experimental data, to have the percent compliance strain at 16 N/cm be between 10% and 30% 157, at least at implantation. As indicated, the implants described herein (and particularly the implants having an ECM substrate in which the compliance control pattern is aligned with the stitching pattern forming the gripping strands) may be within this desired compliance window.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of making an implant having a plurality of gripping strands that enhance the gripping strength of the implant, the method comprising:
    stitching a first pattern into one or more sheets of a substrate material over a mask that is positioned adjacent to a first side of the one or more sheets of the substrate material, wherein the first pattern comprises a continuous first strand of material extending adjacent to a second side of the one or more sheets of the substrate material and a second strand of material extending adjacent to the mask; and
    cutting the second strand of material to release the mask from the one or more sheets of the substrate material and to form a plurality of gripping strands extending proud of the first side of the one or more sheets of the substrate material, wherein each gripping strand of the plurality of gripping strands comprises one or more arms extending from a vertex in which the gripping strand is wrapped around the continuous first strand of material extending adjacent to the second side of the one or more sheets of the substrate material.

2. The method of claim 1, further comprising stitching a first compliance control pattern into the one or more sheets of the substrate material.

3. The method of claim 2, wherein stitching the first compliance control pattern comprises stitching a grid pattern.

4. The method of claim 2, wherein the first compliance control pattern is stitched before stitching the first pattern.

5. The method of claim 2, wherein the first compliance control pattern and the plurality of gripping strands are arranged and configured so that the implant has a peak compliance strain at a load of 16 Newtons per centimeter (N/cm) that is between 10% and 30%.

6. The method of claim 1, wherein stitching the first pattern into the one or more sheets of the substrate material comprises stitching the first pattern into one or more sheets of extracellular material (ECM).

7. The method of claim 1, further comprising forming an anchor at an end of each arm of the one or more arms that is opposite from the vertex, wherein the anchor is formed when cutting the second strand of material.

8. The method of claim 1, wherein the mask comprises a mesh.

9. The method of claim 1, wherein cutting the second strand of material comprises cutting the second strand of material so that each of the one or more arms of each gripping stand is between 3 mm and 0.1 mm long.

10. The method of claim 1, wherein stitching the first pattern comprises stitching the first and second strands of material to form a density of gripping strands between 5-50 gripping strands per $cm^2$.

11. The method of claim 1, wherein the plurality of gripping strands are formed of a resorbable material.

12. A method of forming an implant comprising a plurality of gripping strands extending proud of a first side of the implant to increase a gripping strength of the first side, the method comprising:
    stitching a first grid pattern into one or more sheets of extracellular material (ECM);
    stitching a back-and-forth pattern into the one or more sheets of ECM over a mask on the first side of the ECM, wherein the back-and-forth pattern comprises a continuous first strand of material extending adjacent to a second side of the ECM and a continuous second strand of material extending adjacent to the first side of the ECM;
    cutting the continuous second strand of material to remove the mask and form a plurality of gripping strands extending proud of the first side of the ECM, wherein each gripping strand of the plurality of gripping strands comprises one or more arms extending from a vertex that is wrapped around the continuous first strand of material extending on the second side of the ECM; and
    forming an anchor at an end of each of the one or more arms opposite from the vertex.

13. The method of claim 12, wherein the first grid pattern is stitched before the back-and-forth pattern.

14. The method of claim 12, wherein the first grid pattern is stitched after cutting the continuous second strand of material.

15. The method of claim 12, wherein the anchor is formed by heating the end of each arm of the one or more arms.

16. The method of claim 12, wherein the anchor is formed when cutting the continuous second strand of material.

17. The method of claim 12, wherein forming the anchor comprises forming a knob-shape at the end of each arm of the one or more arms.

18. The method of claim 12, wherein the plurality of gripping strands comprises a plurality of V-shaped griping strands.

19. The method of claim 12, wherein each of the one or more arms of each gripping stand comprises a tilt angle relative to the second side of the ECM that is between about 80 and about 50 degrees.

20. The method of claim 12, wherein the sheet of ECM comprises collagen.

21. The method of claim 12, wherein the one or more sheets of ECM is a first one or more sheets of ECM, wherein the implant further comprises a second one or more sheets of ECM layered onto the first one or more sheets of ECM, wherein the first grid pattern and the back-and-forth pattern are stitched through both the first and second one or more sheets of ECM.

22. The method of claim 12, wherein the plurality of gripping strands are arranged and configured so that the gripping strength of the implant is greater than at least twice a gripping strength of the sheet of ECM without the plurality of gripping strands.

\* \* \* \* \*